(12) United States Patent
Shin et al.

(10) Patent No.: US 6,812,214 B2
(45) Date of Patent: Nov. 2, 2004

(54) USE OF HARPAGID-RELATED COMPOUNDS FOR PREVENTION AND TREATMENT OF OSTEOPOROSIS, ARTHRITIS AND RUPTURED DISC AND PHARMACEUTICAL COMPOSITION CONTAINING THE SAME

(75) Inventors: Joon Shik Shin, Hospital of Jaseng Oriental Medicine, 635, Shinsa-dong, Kangnam-ku, Seoul (KR); Sang Tae Kim, Seoul (KR); Yong Nam Han, Seoul (KR)

(73) Assignee: Joon Shik Shin, Seoul (KR)

( * ) Notice: Subject to any disclaimer, the term of this patent is extended or adjusted under 35 U.S.C. 154(b) by 0 days.

(21) Appl. No.: 09/995,691

(22) Filed: Nov. 29, 2001

(65) Prior Publication Data
US 2002/0183264 A1 Dec. 5, 2002

(30) Foreign Application Priority Data
Nov. 29, 2000 (KR) ......................... 2000-71497

(51) Int. Cl.⁷ ................ A61K 31/7048; C07H 17/04
(52) U.S. Cl. ................ 514/27; 514/26; 514/108; 514/456; 536/1.11
(58) Field of Search ................ 514/27; 424/195.1

(56) References Cited

U.S. PATENT DOCUMENTS 6,280,737 B1 * 8/2001 Stumpf et al. ............... 424/769

FOREIGN PATENT DOCUMENTS

GB 2335919 A * 10/1999 ............ C07H/17/04

OTHER PUBLICATIONS

Chrubasik, S. et al "Treatment of rheumatic pain with kampo medicine in Europe. Part 1. *Harpagophytum procumbens*", Pain Clinic, 1999, vol. 11, No. 3, pp 171–178.*

Recio, Del Carmen et al "Structural considerations on the iridoids as anti–inflammatory agents", Planta Medica, 1994, vol. 60, No. 3, pp 232–234.*

Kikuchi, Tohru et al "New Iridoid Glucosides from *Harpagophytum procumbens* DC", Chem. Pharm. Bull., 1983, vol. 31, No. 7, pp 2296–2301.* von H. Lichti et al "Die Structur des Harpagosids", Helvetica Chimica Acta, 1966, 49, 1552–1580.*

Benito et al, Planta Medica, 200, 66, 324–328.*

* cited by examiner

*Primary Examiner*—James O. Wilson
*Assistant Examiner*—Ganapathy Krishnan
(74) *Attorney, Agent, or Firm*—Birch, Stewart, Kolasch & Birch LLP

(57) ABSTRACT

In the present invention, it is discovered that a compound of formula (I) has a potent effect for treatment of osteoporosis, arthritis and ruptured disc:

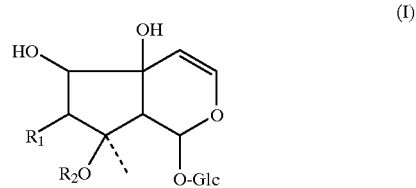

(I)

in which $R_1$ represents hydrogen atom or alkyl group and $R_2$ represents hydrogen atom r cinnamoyl group. Therefore, the compound of formula (I) can be used for prevention and treatment of osteoporosis, arthritis and ruptured disc. Thus, the present invention provides a pharmaceutical preparation containing as an effective component a compound of formula (I) in combination with a pharmaceutically acceptable auxiliary, diluent, isotonic agent, preservative, lubricant and solubilizing aid, which is formulated in the form of a pharmaceutically acceptable preparation and has a potent effect for osteoporosis, arthritis and ruptured disc.

3 Claims, 17 Drawing Sheets synovial cell culture from rheumatoid arthritis (Ra)

Angiogenic inhibitory effect in CAM by CBB-13/LNE-3

Inhibitory effect of cartilagedegration in joint bone

Mophology pattern of murine macrophage

Apoptosis of synovial fibroblast cell

INHIBITORY EFFECT OF COX-II EXPRESSION BY SDS-PAGE

PHOTOGRAPHY OF X-RAY AFTER DRUG DOSE

REPAIR EFFECT OF RUPTURED DISC

BEFORE　　　　　　　　　　　　　　AFTER

USE OF HARPAGID-RELATED COMPOUNDS FOR PREVENTION AND TREATMENT OF OSTEOPOROSIS, ARTHRITIS AND RUPTURED DISC AND PHARMACEUTICAL COMPOSITION CONTAINING THE SAME

TECHNICAL FIELD

The present invention relates to a use of a harpagid-related compound as an agent for treating arthritis, osteoporosis and ruptured disc, and to a pharmaceutical composition containing said harpagid-related compound as an effective component.

BACKGROUND ART

At present, it has been known that in Korea patients suffering from various bone diseases are on an increasing tendency annually. However, chemotherapy, operative therapy, etc. which have been currently used for the purpose of treating bone diseases have fail to realize the complete success as yet. Such bone diseases are advanced to chronic and degenerative state due to ageing, and further impose a great medical burden on a patient. Therefore, the development of novel materials which can be generally utilized in the clinical field is still urgently required.

It has been known that rheumatoid arthritis and degenerative arthritis known as typical adult diseases and geriatric diseases are an intractable disease (FIG. 2a), and are caused by a mechanism based on the activation of synovial cells in joint and the ageing due to such activation and the autoimmunological factors (FIG. 2b). It is expected that rheumatoid arthritis and degenerative arthritis can be cured by development of a drug which can kill or inhibit arthritic cells or inhibit or repress the expression of cyclooxygenase II (COX-II) as the enzyme produced by such arthritic cells (FIG. 2c).

The constituent drugs contained in the galenic composition developed by the resent inventors have been described in "Dongeubogam" and "Sinnongbonchokyung" as having various pharmacological activities including hematopoiesis, tonic, diuresis, bone marrow formation, recruitment of vitality and virility, effects on pre- and post-partum joint, lumbago, stomachic, anti-inflammatory, promotion of blood circulation and removal of blood stasis, elimination of nervous disorders, detoxication, hemostasis, effect of alleviating climacteric disorders, ernmenagogic effect, nutritive effect, hematic activity, etc. Further, other activities have also been disclosed in prior reference.

Throughout the whole world, the study of bone diseases has been actively conducted, and as a result, according to an increase of a series of immunological knowledge the etiology and mechanism of arthritic invasion have been revealed so that some agents for treatment of osteoporosis have been developed in recent days. Specifically, allendrate, tamoxifen, vitamin $D_3$, parathyroid hormone (PTH) and COX-II inhibitor as an agent for treatment of rheumatoid arritis have already been successfully commercialized. Further, as an anti-inflammatory agent sulfasalazine (Becker K, Gromer S, Schirmer R H, Muller S., Thioredoxin reductase as a pathophysiological factor and drug target. Eur. J. Biochem., 2000 Oct., 15; 267(20):6118–6125) and thioredoxin reductase (a pathophysiological factor and drug target. Eur. J. Biochemn., 2000 Oct., 15; 267(20):6118–6125) have been known and are under either clinical trials or research and development. Meanwhile, as an agent for treatment of osteoporosis alendronate, raloxifene, calcitonin (Moraghan T J, Perez EA. Mayo Clin Proc. 2000 August; 75(8):821–9), estradiol (An-dersson T L, Stehle B, Davidsson B, Hoglund P. Maturitas. 2000 Jun. 30; 35(3):245–52), genistein (Mazurek A P, Polkowski K, Acta Pol Pharm. 2000 March–April; 57(2):135–55), 1,25-dihydroxyvitamin $D_3$ (Am. J. Physiol. Endocrinol. Metab. 2000 July; 279(1):E213–20), patathyroid hormone (Hunziker 3, Wronski T J, Miller S C, J. Dent. Res. 2000 June; 79(6):1431–8), alendronate (Kashyap A S, Kashyap S. Postgrad Med J. 2000 July; 76(897):417–8), estrogen receptor modulators, calcitonin, and bisphosphonates (Wimal-Awansa S J. J. Clin. Densitom. 2000 Summer; 3(2):187–201) have been also disclosed.

Thus, in consideration of the problems caused in applying the prior drugs for the clinical purpose and involved in the toxic side effects, the present inventors have obtained the solvent fractions of *Harpagophytum procumbens* DC as one of medicinal plants and observed the inhibitory activity of respective fractions against proliferation of synovial cells in joint portion. As a result, we have demonstrated that ethyl acetate fraction (LNE fraction) and butanol fraction (LNB fraction) of *Harpagophytum procumbens* DC are effective.

*Harpagophytum procumbens* DC is a medicinal plant belonging to Pelaliacease, which inhabits the Kalahari Desert of Africa and is also called 'Devil's claw' and of which rhizoma has been used for arthritis as a popular remedy in Africa and Europe [Schmidt, S.; Rothenfelde, B., The great significance of Harpagophytum root. Zeitschrift f ür Naturhcilkunde. 22, 48(1978); Seeger, P. C., Harpagophytum, an effective plant remedy, Effahrungsheilunde, vol. 8, 1978. Soulimani, R.; Younos, C.; Mortier, F.; Derrieu, C., The role of stomachal activity of plant extracts, using as an example extracts of *Harpagophytum procumbens*. Canad J. Physiol. Pharm. 72(12), 1532]. It has been known that *Harpagophytum procumbens* DC contains harpagide, harpahoside, procumbide [Kapf, R., Schweiz. Apoth.-Ztg., 114, 377(1976); Sticher, O., Dtsch. Apoth.-Ztg., 117. 1279(1977); Caprasse, M., J. Pharm. Belg., 35, 143(1980)], 8-O-(p-coumaroyl)-harpagide, 6-O'-(p-coumaroyl)-procumbide and procumboside [Kikuch, Tohri; Matsuda, Satoko; Kubo, Yoko; Namba, Tsuneo, New iridoid glucosides from *Harpagophytum procumbens* DC. Chem. Pharm. Bull., 31(7), 2296(1983)]. However, no pharmacological activity has been known for the above components as yet.

The present inventors combined ethyl acetate fraction (LNE fraction) and butanol fraction (LNB fraction) as the effective fractions of *Harpagophytum procumbens* DC and then treated the mixture with silica gel chromatography to separate and purify LN-1, LN-2 and LN-3, respectively. As a result from determination of their chemical structures, it was identified that LN-1 is harpagoside, LN-2 is starchyose and LN-3 is harpagide. Harpagoside and harpagide are the compounds, which were already reported as being separated from *Harpagophytum procumbens* DC [von H. Lichti; A. von Wartburg, Die struktur des Harpagosides. Helvetica Chinica Acta, 49, Fasciculus 5, 1552(1996)], and starchyose is a kind of tetrasaccharides, which is contained in cotton seed and soybean in a relatively large quantity (Dong-Hoon, Kim, Food Chemistry, p185, 1978, Tamgudang), and was first isolated from *Harpagophytum procumbens* DC by the present inventors.

The present inventors have examined the effect on arthritis of the compounds isolated and purified from *Harpagophytum procumbens* DC. As a result, we have demonstrated that LN-3 (harpagide) is most effective and LN-1 (harpagoside) has a moderate pharmacological effect. Further, although it was already reported that harpagoside is heated under alkaline condition to produce harpagide [Kikuchi, Tohru; Matsuda, Satoko; Kubo Yoko; Namba, Tsuneo, New iridoid glucosides from *Harpagophytum procumbens* DC. *Chem. Pharm. Bull.*, 31(7), 2296(1983)], the present inventors obtained the result that harpagide can be obtained from harpagoside even at room temperature without heating under alkaline condition.

However, the prior art did never disclose that harpagoside and harpagide have an anti-arthritic effect and an effect of treating osteoporosis and ruptured disc.

DISCLOSURE OF INVENTION

The present inventors have discovered the fact that the known compounds, harpagide and harpagoside, as the constituents of *Harpagophytum procumbens* DC exhibit a very potent anti-arthritic effect and also have an effect on osteoporosis, and thus, completed the present invention.

Therefore, the object of the present invention is to provide the pharmacological use of a harpagide-related compound represented by the following formula (I), in treating arthritis, osteoporosis and ruptured disc:

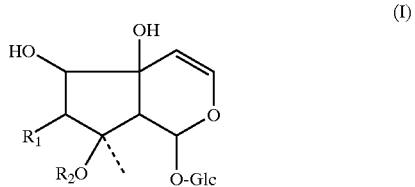

in which $R_1$ represents hydrogen atom or alkyl group; and $R_2$ represents hydrogen atom or cinnamoyl group.

In the above formula (I), the compound wherein $R_1$ is methyl and $R_2$ is cinammoyl is harpagoside and the compound wherein $R_1$ is methyl and $R_2$ is hydrogen atom is harpagide.

Further, another object of the present invention is to provide a pharmaceutical composition containing the compound of formula (I) above as a major component.

Still another object of the present invention is to provide a process for converting harpagoside having a relatively weak pharmacological effect into harpagide having a relatively potent pharmacological effect.

BRIEF DESCRIPTION OF THE DRAWINGS

The above objects and other advantages of the present invention will become more apparent by describing in detail of preferred embodiment thereof with references to attached drawings, in which.

BEST MODE FOR CARRYING OUT THE INVENTION

Figure 1A:
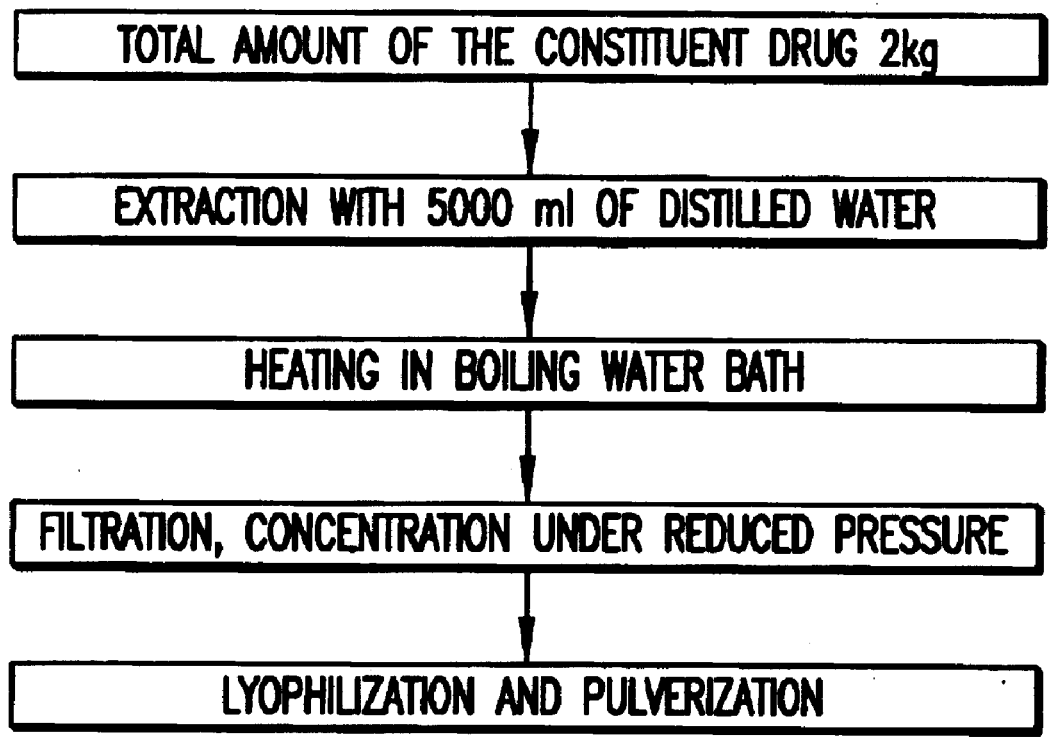
FIG. 1 shows (a) the flowchart of a process for recovering the dry weight of the pharmaceutical composition by extraction of the constituent drug with distilled water and an organic solvent, concentration under reduced pressure and lyophilization, and (b) the flowchart of the procedures for extracting the organic fraction according to the process for extracting the effective component.
Figure 1B:
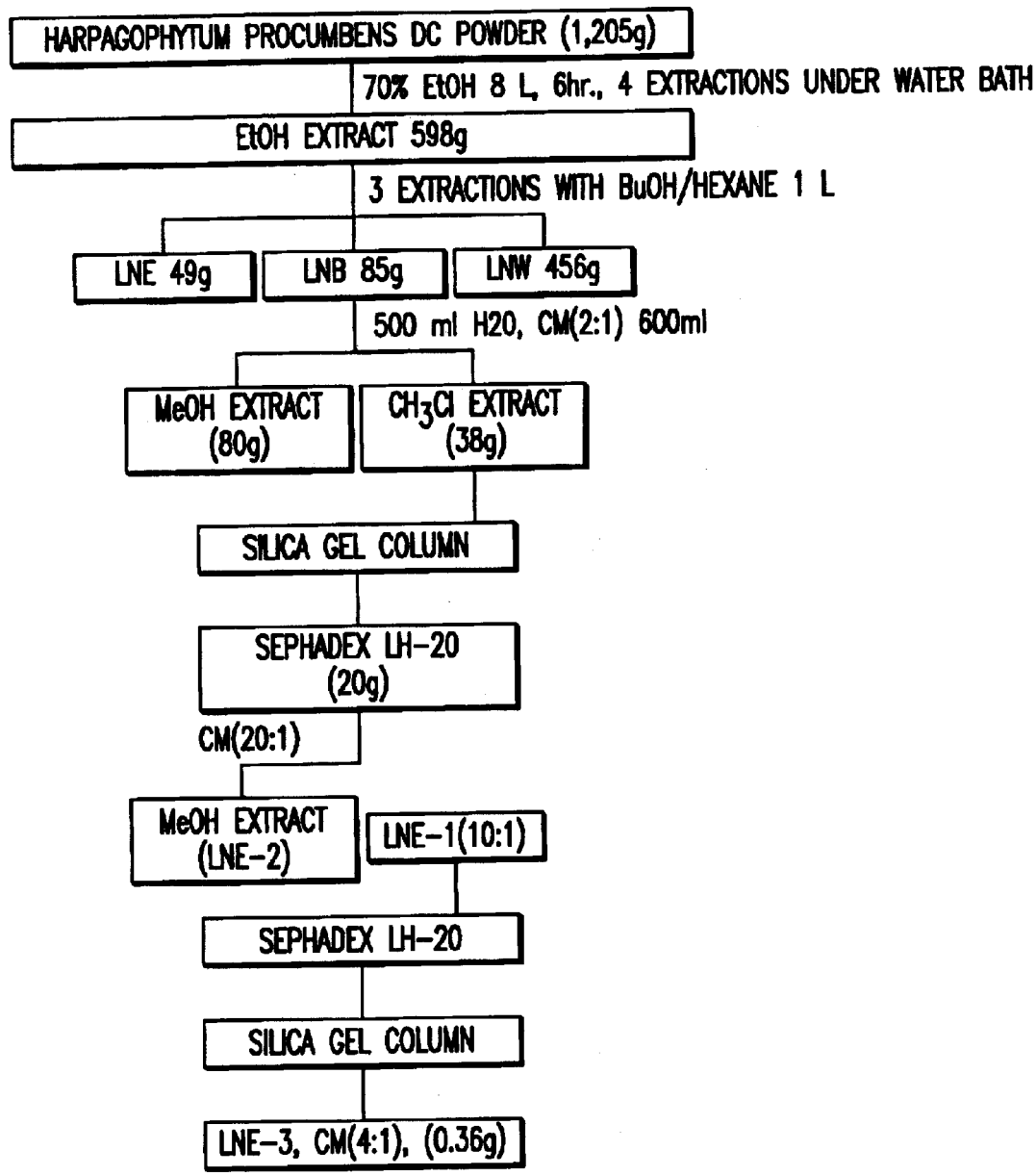
Figure 2A:
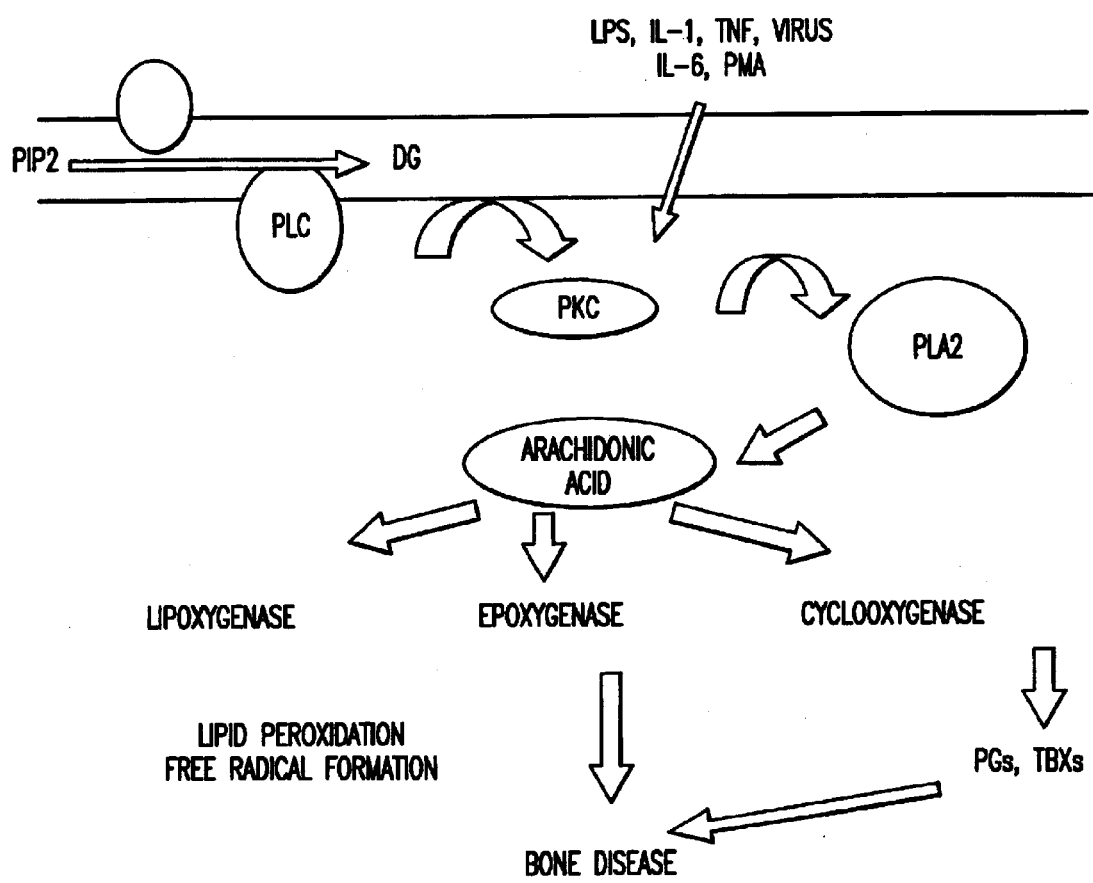
FIG. 2 shows (a) the causal mechanism of invasion, (b) the invaded portions, and (c) the route for transmitting molecular biological signals of invasive process in joint at which arthritis as the typical one of bone diseases is invaded.
Figure 2B:
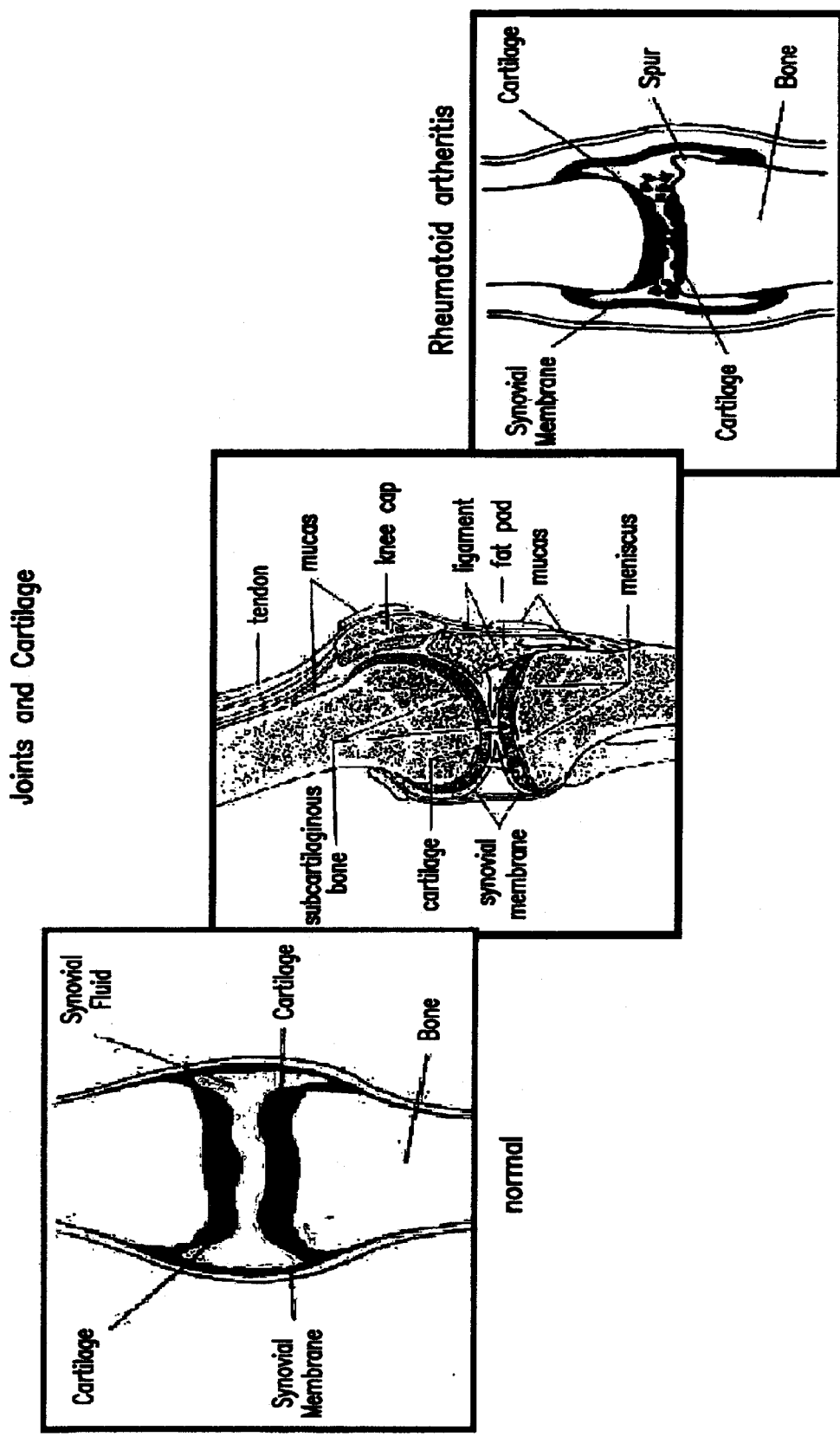
Figure 2C:
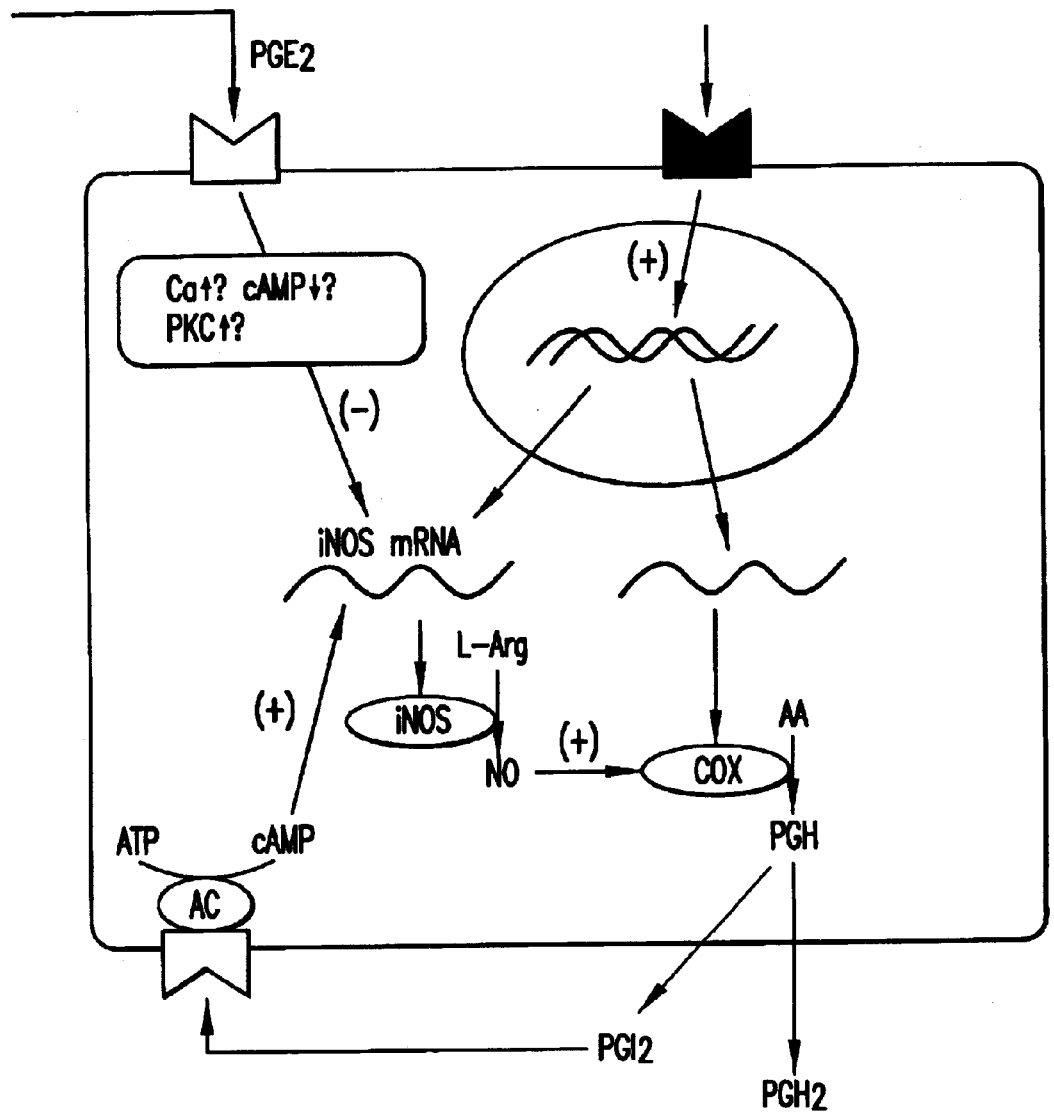

The present invention will be more specifically illustrated by the following examples and experiments. However, it should be understood that these examples and experiments do not intend to limit the scope of the present invention in any manner.

EXAMPLE 1

8 Liters of 70% ethanol was added to 1,205 g of *Harpagophytum procumbens* DC, which was then extracted 4 times for 6 hours each time in a water bath. The combined extracts were evaporated to obtain 598 g of the extract of *Harpagophytum procumbens* DC.

The resulting extract was suspended in 1 ml of water and then successively extracted with hexane (1 liter×3) and butanol (1 liter×3). The respective extracts were concentrated under reduced pressure. The yields of ethanol extract and solvent fractions are 598 g, 49 g for LNE, 85 g for LNB and 456 g for LNW, respectively.

EXAMPLE 2

Separation of the Compounds LN-1, LN-2 and LN-3 from LNE and LNB Fractions of *Harpagophytum procumbens* DC 46 g of LNE and 81 g of LNB were combined, suspended in 500 ml of water and then mixed with 600 ml of chloroform/methanol (CM) 2:1 solution. The chloroform layer was collected. The residue was extracted further two times with CM 2:1 solvent and the chloroform layer was collected. The chloroform layers were combined and then concentrated to obtain 38 g of the extract (Fraction 1). The aqueous layer was concentrated to obtain about 80 g of the extract (Fraction 2). The chloroform extract (Fraction 1) was purified on silica gel column and then re-purified with Sephadex LH-20 (methanol solvent) to obtain the compound (12 g). The aqueous layer (Fraction 2) was subjected to chromatography on silica gel column using CM 20:1 →10:1→8:1→4:1→2:1 and methanol solvent. The compound LN-1 (5.1 g) was obtained from the eluate with CM 10:1 eluent. The methanol eluates were combined (6.5 g) and then subjected to chromatography on Sephadex LH-20 column using 50% aqueous acetone solution (×3) ad water as the solvent to obtain the compound LN-2 (4.5 g).

The eluates with CM 4:1 eluent were again combined and then subjected to chromatography on silica gel column using CM 4:1 to obtain the compound LN-3 (0.36 g). The resulting compounds LN-1, LN-2 and LN-3 were harpagoside, starchyose and harpagide, respectively.

1) LN-1 (harpagoside)

Melting point: 120° C. (amorphous)

MS m/z(%): 148 ([$C_9H_8O_2$]$^+$, 74.8), 147 (79.1), 77 (100)

IR$\nu_{max}^{KBr}$ (cm$^{-1}$): 3430 (OH), 1690(C=O), 1638 (C=C), 1578, 1561, 1543, 1508, 1499 (benzene), 1186, 1119, 1074, 1015 (C—O), 990, 955 (CH=CH, trans), 770, 716, 685 (CH=CH, cis)

$^1$H-NMR (CD$_3$OD) δ: 1.53 (3H, s, 10-H$_3$), 2.02 (1H, dd, J=4.2, 15 Hz, 7-H), 2.27 (1H, dt, J=15, 1.2 Hz, 7-H), 2.94 (1H, br.s, 9-H), 3.22 (1H, dd, J=7.8, 9.0 Hz, glc-2), 3.35 (1H, d-like, J=9.9 Hz, glc-4), 3.36 (2H, ddd, J=2.1, 5.1, 10 Hz, glc-5), 3.41 (1H, dd, J=8.7, 9.3 Hz, glc-3), 3.72 (1H, dd, J=5.7, 12 Hz, glc-6), 3.76 (1H, dd, J=1.2, 4.2 Hz, 6-H), 3.93 (1H, dd, J=2.4, 12 Hz, glc-6), 4.62 (1H, dd, J=8.1 Hz, glc-1), 4.94 (1H, dd, J=1.5, 6.3 Hz, 4-H), 6.18 (1H, d, J=1.2 Hz, 1-H), 6.41 (1H, d, J=6.3 Hz, 3-H), 6.51 (1H, d, J=15.9 Hz, C=CH—C=O), 7.38–7.42 (3H, m, benzene-3H), 7.6–7.61 (2H, m, benzene-2H), 7.67 (1H, d, J=15.9 Hz, CH=C—C=O)

2) LN-2 (starchyose)

Melting point: 148° C.

[α]$_D^{25}$: +138.6

$^1$H-NMR (D$_2$O) δ: 3.33 (2H, s, β-Fru(f)-H$_2$), 4.20 (1H, d, J=9.0 Hz, β-Fru(f)-3H), 4.97 (2H, d, J=2.4 Hz, 2×α-Gal(p)-anomeric proton), 5.41 (1H, d, J=3.9 Hz, α-Glu(p)-anomeric proton) (wherein β-Fru(f) means β-fructofuranosyl; α-Gal (p) means α-galactopyranosyl; and α-Glu(p) means α-glucopyranosyl)

$^{13}$C-NMR (D$_2$O) δ: see Table 1

TABLE 1

Nuclear magnetic resonance (NMR) data of LN-2 (starchyose)

| Position | LN-2 | Standard sucrose | Position | LN-2 | Standard □-Gla(p) |
|---|---|---|---|---|---|
| α-Glu(p) | | | α-Gal(p) | | |
| 1 | 92.86 | 92.89 | 1" | 99.13 | 93.7 |
| 2' | 70.25 | 71.79 | 2" | 69.20 | 69.9 |
| 3' | 73.48 | 73.30 | 3" | 70.25 | 70.2 |
| 4' | 69.56 | 69.95 | 4" | 70.10 | 70.2 |
| 5' | 72.04 | 73.12 | 5" | 71.75 | 71.7 |
| 6' | 66.63 | 62.09 | 6" | 67.24 | 62.5 |
| β-Fru(f) | | | α-Gal(p) | | |
| 1 | 63.22 | 63.08 | 1''' | 98.79 | 93.7 |
| 2 | 104.56 | 104.41 | 2''' | 69.04 | 69.9 |
| 3 | 82.10 | 82.09 | 3''' | 70.13 | 70.2 |
| 4 | 74.76 | 74.73 | 4''' | 70.00 | 70.2 |
| 5 | 77.12 | 77.16 | 5''' | 71.44 | 71.7 |
| 6 | 61.90 | 60.85 | 6''' | 62.20 | 62.5 |

Complete Acid Hydrolysis of LN-2

2.4 ml of 4N HCl/dioxane/benzene (3:1:2) mixed solution was added to LN-2 (20mg) and the mixture was heated at 100° C. for one hour. The reaction solution was cooled and the aqueous layer was subjected to TLC on silica gel plate using chloroform/methanol/water (30:20:5) as the solvent. As a result, it could be identified that fructose/glucose/galactose are present in the ratio of 1:1:2.

Partial Acid Hydrolysis of LN-2

5.0 ml of 2N HCl/dioxane/benzene (3:1:2) mixed solution was added to LN-2 (500 mg) and the mixture was heated at 93° C. for 40 minutes. The reaction solution was cooled and then concentrated. The residue was molecular filtered through Sephadex G-25 (solvent: 5% ethanol) and lyophilized to obtain LN-21 (120 mg). LN-21 was completely hydrolyzed according to the same manner as above and then subjected to TLC. As a result, fructose was not detected and only glucose and galactose were detected.

LN-21 (α-D-galactopyranosyl(1"→6')-α-D-galactopyranosyl(1'→6)glucopyranoside)

$^1$H-NMR(D$_2$O) δ: 4.66 (d, J=8.1 Hz, β-Glu(p)-anomeric proton), 4.98 (2H, m, 2×α-Gal(p)-anomeric proton), 5.23 (d, J=3.6 Hz, α-Gal(p)anomeric proton) (4.66 ppm area/5.23 ppm area ratio=2.14)

3) LN-3

Melting point: 120° C. (amorphous)

$^1$H-NMR(CD$_3$OD) δ: 1.24 (3H, s, 10-H$_3$), 1.79 (1h, ddd, J=0.9, 4.2, 13.8 Hz, 7□-H), 1.90 (1H, dd, J=4.8, 13.8 Hz, 7□-H), 2.54 (1H, br.s, 9-H), 3.21 (1H, dd, J=7.8, 9.0 Hz, 2'-H), 3.31 (1H, 4'-H), 3.34 (1H, m, 5'-H), 3.38 (1H, t, J=9.0 Hz, 3'-H), 3.66 (1H, dd, J=5.7, 12.0 Hz, 6'-H), 3.70 (1H, t-like, J=~4.5 Hz, 6-H), 3.90 (1H, dd, J=1.5, 12.0 Hz, 6'-H), 4.57 (1H, d, J=7.8 Hz, 1'-H), 4.94 (1H, dd, J=1.5, 6.3 Hz, 4-H), 5.73 (1H, d, J=0.9 Hz, 1-H), 6.31 (1H, d, J=6.6 Hz, 3-H)

EXAMPLE 3

Preparation of Harpagide (LN-3) from Harpagoside (LN-1)

560 mg of harpagoside (LN-1) was dissolved in 20 ml of methanol, mixed with 1 ml of 1N sodium hydroxide, allowed to stand overnight at room temperature and then passed through Sephadex LH-20 (solvent: 80% methanol) column. 400 mg of harpagide and 125 mg of sodium cinnamate were obtained from the eluate.

EXAMPLE 4

Instead of 1N sodium hydroxide 2% aqueous sodium carbonate solution was added according to the same procedure as Example 3, and then the procedure was conducted according to Example 5 to obtain harpagide and sodium cinnamate.

EXAMPLE 5

Mass Production of Harpagide from *Harpagophytum procumbens* DC 1 kg of *Harpagophytum procumbens* DC powder was extracted four times with 20 liters of methanol at room temperature and the extracts were combined and then concentrated under reduced pressure. 475 g of the resulting methanol extract was dissolved in 1.5 liters of purified water, extracted three times with 1.5 liters of hexane, well mixed with 0.1 liters of 5% aqueous sodium hydroxide solution (pH 11.5–12.5) and then allowed to stand overnight at room temperature. The reaction solution was extracted two times with 2 liters of isopropyl alcohol each time. The isopropyl alcohol fractions were combined, washed with 1 liter of purified water and then concentrated under reduced pressure to obtain 15 g of the powder. The resulting powder was subjected to chromatography on Sephadex LH-20 column (size 10×100 cm) equilibrated with 95% ethanol. The fractions eluting harpagide (silica gel thin layer chromatography, solvent: chloroform/methanol/water 70:30:4, Rf value=0.31) were combined and then concentrated to obtain 12 g of harpagide.

Experiment 1

Inhibitory Effect on Edema of Arthritis

In order to observe the inhibitory effect on edema of the pharmaceutical composition of the present invention, 6 albino rats weighing 200 g were used per test group to induce edema by injecting the mixture of 0.5 ml of Zymosan-A (20 mg/ml/kg) and 0.5 ml of Freund's adjuvant into ST36 position of left paw and then observed for the progress of edema for 70 days by taking a photograph before and after induction of edema. The water extract and organic solvent fractions of the pharmaceutical composition of the present invention were respectively constituted in the concentration of 0.6 mg/ml and then orally administered for 14 days to albino rats in an amount of 1 ml per kg of body weight once a day to determine the inhibitory effect on edema. As the test sample, the organic solvent fractions of the pharmaceutical composition including ABE, ABB, ABW, CBE, CBB, CBW, LNE, LNB, LNW, CRB, CRW, SSH and SSW were respectively used. As the result of this test, it was observed that edema was started to induce on day 4 and reached the peak point after about 45 days. The period for this test was established as 70 days after edema induction to observe the inhibitory effect on edema of the extracts of the present invention. As the result, the edema size was measured using a precision gauge.

Experiment 2

Determination on Survival of Synovial Cells in Rheumatoid Arthritis

The synovial cells separated from outpatients suffering from rheumatoid arthritis were distributed on 5% DMEM medium supplemented with penicillin/streptomycin in a 6-well culture dish at the concentration of $10^4$ cells and then incubated for 24 hours at 37° C. to observe the surviving cells. In order to determine the presence or absence of cells and the proliferating state of cells, apoptosis-induced cells were examined by taking their photographs under a phase-contrast microscope of 200 magnifications.

Experiment 3

Induction of Angiogenesis of Synovial Cells in Chorioallantoic Membrane of Fertilized Egg In order to determine the effect of the organic solvent fractions obtained in Experiment 1 on the angionenesis of synovial cells using the cells separated in Experiment 2, synovial cells were injected into fertilized egg and then incubated in an incubator at 37° C. for 3 days to observe the formation of chorioallantoic membrane (CAM). In the present state, the fractions separated according to the above method were respectively distributed on CAM at the concentration of 10 μg/ml to observe the degree of CAM decrease.

Experiment 4

Determination on the Rupture Extent of Cartilaginous Tissue in Arthritic Tissue

In order to determine the abrasion extent of cartilage present in point portion and the rupture extent of cartilaginous tissue and cartilaginous cells due to secretion of metalloprotease by orally administering the water extract as the pharmaceutical composition used in Experiment 1, the cartilage portion was stained with hematoxylin/eosin, observed by means of a phase-contrast microscope of 200 magnifications and then photographed.

Experiment 5

Determination on the Extent of NO Formation in Macrophage Cells Stimulated by Lipid Polysaccharide In order to identify whether the extracts obtained according to the present invention can inhibit the synthesis of nitric oxide (NO) as the potent inducer of inflammation in blood due to edema as above, macrophage RAW 264.7 cell lines were distributed in a 96-well microplate at the concentration of $10^3$ cells per well and then incubated for 12 hours. Then, lipid polysaccharide was added to the plate at the concentration of 50 ng/well to stimulate the cells for 2 hours. The respective organic solvent fractions were added to the plate to the final concentration of 10 μg/ml followed by addition of 50 μl of Greiss reagent solution, and then allowed to react together at room temperature. Then, the absorbance of the plate was measured at 540 nm of ELISA (enzyme-linked immunosorbent assay) reader. For comparative analysis, 0.1, 1, 10, 20, 50, 100, 150 μM sodium nitrite as the standard solution were developed with sodium nitroprusside dihydrate (SNP).

Experiment 6
Determination on Induction of Apoptosis of Macrophages and Synovial Cell Lines In order to determine whether the compound identified as the effective component of the pharmaceutical composition separated according to the present invention can induce the apoptosis of Raw 264.7 cell lines as macrophage involved in inflammatory reaction and synovial cells, the cells were distributed on 5% DMEM medium supplemented with penicillin/streptomycin in a 6-well culture dish at the concentration of $10^4$ cells and then incubated at 37° C. for 24 hours while adding the extractions as above at the concentration of 10 μg/ml to observe the reaction. Apoptosis was examined by taking a photograph of apoptosis-induced cells under a polarizing microscope of 200 magnifications.

Experiment 7
Effect on Cell Cycle of Macrophage Cells and Synovial Cell Lines

Two kinds of cells were incubated as in Experiment 6 and then washed with PBS (phosphate-buffered saline). LPS was distributed on the respective dishes at the concentration of 50 ng/ml to stimulate the cells. Then, the extract according to the present invention was added over 2 hours so as to make the final concentration of 20 μg/ml. The supernatant was removed, washed with PBS and then treated with trypsin. The cells were harvested, introduced into Eppendorf tube and then centrifuged at 1,000 rpm for 5 minutes to remove the supernatant. The residue was fixed with addition of 1 ml of 100% ethanol. At this time, the mixture of 5 μg/ml propidium iodide and RNAse was separately prepared. The fixed cells were centrifuged to remove the supernatant and then washed once with PBS. Simultaneously, the staining agent as previously prepared above was added to the fixed cells and then warmed in an incubator at 37° C. for 30 minutes. The cells stained with propidium iodide was sealed with foil, stored at 4° C. and then subjected to a flow cytometry analysis using FACscan (Becton Dickinson, Calif.) as the analyzing apparatus.

Experiment 8
Inhibition on the Expression of COX-II and iNOS Proteins at the Level of Transcription Through RT-PCR In order to identify the ingredient having an inhibitory activity against COX-II and inducible nitric oxide synthetase (iNOS) as the causal factors of rheumatoid arthritis in the extract used as the effective component of the pharmaceutical composition according to the present invention as in Experiment 6 above, the cells were distributed in T75 flask at the concentration of $10^5$ cells, incubated for 7 days and then stimulated for 2 hours by introducing LPS in the flask at the concentration of 50 ng/ml. Then, the extract of the present invention was added so as to make the final concentration of 50 μg/ml. The cells were harvested into a 1.5 ml Eppendorf tube and centrifuged with 15,000 rpm at 4° C. for 15 minutes to remove the supernatant. 200 μl of RNAzol solution was added to the residue followed by addition of 50 μl of chloroform. The cells were lysed by careful pippeting, and then centrifuged with 15,000 rpm at 4° C. for 15 minutes to recover a total RNA, which was then precipitated at 4° C. for 15 minutes by adding the same volume of isopropanol, washed once with 75% ethanol and then dried. The cell lysate was dissolved by adding 20 μl of RNase free $D_2O$ and then warming the mixture at 60° C. for 30 minutes. Then, reverse transcriptase reaction was conducted at 50° C. for 20 minutes by adding 5 μl of 10 mM dNTP, 6 μl of 25 mM $MgCl_2$, 5 μl of 10× RNA PCR buffer, 1 μl of RNase inhibitor, 1 μl of AMV-optimized Taq, 1 μl of AMV reverse transcriptase XL, 1 μl of 50 pM specific primer (sense/antisense), and 26 μl of RNase free $dH_2O$ to 5 μl of total RNA, and then stopped at 94° C. for 2 minutes to conduct DNA synthetic reaction (polymerase chain reaction: PCR). The PCR was conducted under conditions comprising 94° C. 1 minute, 55° C. 45 seconds, 70° C. 60 seconds for 35 cycles, and then, finally the elongation reaction was conducted at 70° C. for 5 minutes to complete the reaction. The resulting PCR product was eluted on 1% agarose gel and observed whether the bands are present near 395 bp and 278 bp on the basis of a size marker.

Experiment 9
Identification of Expression of COX-II Protein by SDS-PAGE

In order to identify whether the extract obtained by the process according to the present invention inhibits the activity of COX-II, $10^5$ synovial cells isolated from patients suffering from chronic rheumatoid arthritis were distributed in T75 flask, incubated for 7 days and then stimulated for 2 hours by introducing LPS in the flask at the concentration of 50 ng/ml. Then, the extract of the present invention was added so as to make the final concentration of 50 μg/ml. The cells were dissolved with 0.5 ml of a lysis buffer (0.1 M SDS, sodium azide, PMSF, pepstatin, leupstatin, pH 8.0) and then collected in a 1.5 ml Eppendorf tube, activated by heat-treatment with 100° C. boiling water, and then cooled to room temperature for 5 minutes. Then, the cell lysate was electrophoresed on 10% polyacrylamide gel (SDS-PAGE), and then observed by staining and then decoloring with a destaining solution.

Experiment 10
Identification of Expression of COX-II Protein by Immunocytochemical Analysis In order to determine whether the compound identified as the effective component of the pharmaceutical composition separated by the present invention induces an inhibitory effect on COX-II of synovial cells in joint portion, $10^4$ synovial cells were distributed on 5% DMEM medium supplemented with penicillin/streptomycin in 6-well culture dish containing a slimb over glass, incubated for 24 hours at 37° C., during which the extract of the present invention was added to the concentration of 10 μg/ml to observe the reaction. The waste was removed and then, the cells were washed once with PBS, fixed with methanol and then washed with PBS. The cells were labeled with the primary antibody COX-II and then allowed to stand at 4° C. for about one hour. Then, the cells were labeled with a fluorescence (fluorescein isothiocyanate: FITC) as the secondary antibody, allowed to stand for about one hour while masking from light with foil and then observed under a fluorescence microscope.

Experiment 11
Determination of Joint Rupture in Edema-inhibited Albino Rats by X-ray Analysis The respective water extract and organic solvent fractions were orally administered for 14 days at the concentration of 75 μg/ml to investigate their inhibitory effect on edema as in Experiment 1. The test albino rats were anesthetized to take X-ray photograph.

Experiment 12
Observation of Ruptured Disc by CT Photographing Before and After Treatment In order to examine the clinical pharmacological effect of the pharmaceutical composition separated and purified as in Example 2, the water extract according to the present invention was administered for 2 months to a patient suffering from ruptured disc in a daily dosage of 500 mg. Then, the patient was observed by CT photographing before and after treatment with the extract of the present invention.

Experiment 13
Observation of Ruptured Disc by MRI Photographing Before and After Treatment In order to examine the clinical pharmacological effect of the pharmaceutical composition separated and purified as in Example 2, the water extract according to the present invention was administered for 2 months to a patient suffering from ruptured disc. Then, the patient was observed by MRI photographing before and after treatment with the extract of the present invention.

Experiment 14
Therapeutic Effect on Vertebral Neuroparalysis

In order to examine whether the compound separated in Example 2 inhibits neuroparalysis induced by nogo-A in bone diseases, glioblastoma cell line U-373 MG originated from brain, which was obtained from Korean Cell Line Bank (KCLB) was distributed on 10% DMEM medium supplemented with penicillin/streptomycin in 6-well culture dish at the concentration of $10^4$ cells, incubated at 37° C. for 24 hours and then stably transfected with a vector well expressing nogo-A to observe and identify whether neurites are reduced or their elongation is inhibited. Simultaneously, it was also observed whether neurites can be regenerated by treatment with neuronal growth factor (NGF) or whether the fractions of the present invention can provide the same effect, by taking a photograph with a phase-contrast microscope of 200 magnifications.

Experiment 15

Figure 3:
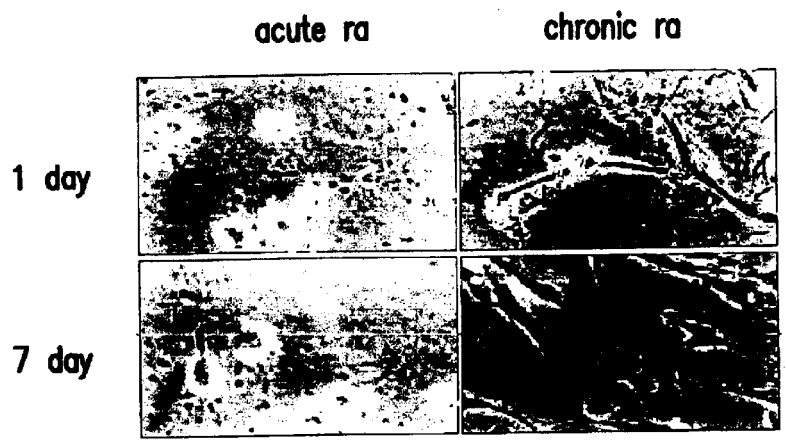
FIG. 3 shows the survival and cytomorphological appearance of synovial cells in joint portion at which arthritis as the typical chronic and degenerative bone diseases is invaded.

As the result of observation in the container incubated as in Experiment 2, in a patient suffering from degenerative arthritis one day after incubation the cells were not grown, the adherent cells were not present in a macroscopic view, and the cells were present in a suspended state. In case of the cells isolated from a patient suffering from chronic arthritis, it could be observed by a phase-contrast microscope of 200 magnifications that the cells were well grown and proliferated after 7 days have passed. Therefore, it could be noted that in case of a patient suffering from degenerative arthritis whole synovial membrane did not cover cartilage tissue and were abraded to cause the absence of synovial cells thereby further stimulating the rupture of cartilage tissue. Contrary to this, in case of a patient suffering from chronic arthritis the proliferation of synovial cells was abnormally progressed due to inflammation and autoimmunity (FIG. 3).

Experiment 16

Figure 4:
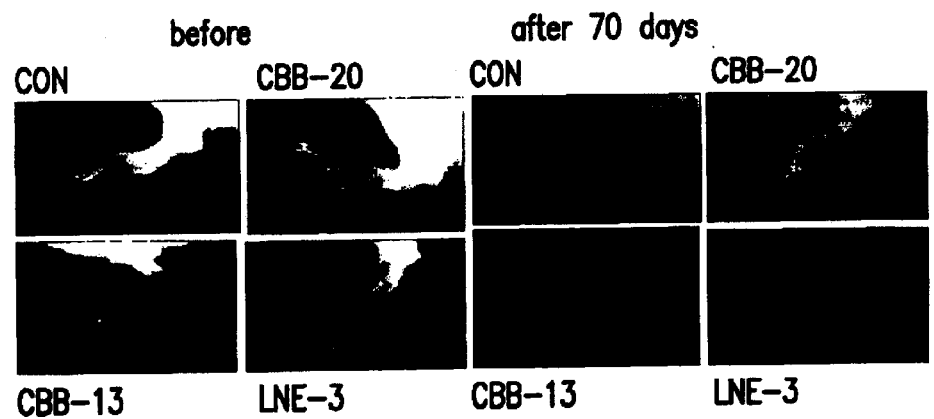
FIG. 4 shows the 70-days inhibitory effect on edema as one of chronic and degenerative osteopathological symptoms of arthritis by treating the induced edema with respective fractions obtained as the organic solvent fractions of the pharmaceutical composition in an amount of 75 µg/ml for 2 weeks via oral route.

When respective fractions separated according to the present invention were applied to the test for edema induction, LNE-1 and 3 exhibited a potent inhibitory effect on edema, and particularly, LNE-3 is most significant. The inhibitory effect on edema of the compound according to the present invention as measured after 70 days have passed are listed in the following Tables 2 and 3 and FIG. 4.

TABLE 2

Inhibitory effect on edema of respective organic solvent fractions (Unit: mm)

| Sample | Before treatment | After treatment | Sample | Before treatment | After treatment |
|---|---|---|---|---|---|
| ABE | 15.5 ± 2 | 8.5 ± 2 | LNB | 15.6 ± 1 | 5 ± 1 |
| ABB | 14.6 ± 3 | 10.1 ± 1 | LNW | 14.5 ± 2 | 8 ± 1 |
| ABW | 14.4 ± 1 | 12.2 ± 2 | CRB | 15.5 ± 1 | 9 ± 2 |
| CBE | 16.3 ± 2 | 4.1 ± 1 | CRW | 15.6 ± 1 | 9 ± 1 |
| CBB | 14.6 ± 1 | 3.6 ± 1 | SSH | 14.5 ± 2 | 12 ± 2 |
| CBW | 15.5 ± 2 | 7.2 ± 2 | SSB | 13.3 ± 1 | 13 ± 1 |
| LNE | 14.5 ± 3 | 5.3 ± 1 | SSW | 14.4 ± 2 | 13 ± 1 |

TABLE 3

Organic solvent fractions having the best inhibitory effect on edema

| Fraction sample | Before treatment | After treatment |
|---|---|---|
| CBB | 14.6 ± 2 | 3.6 ± 1 |
| CBB-13 | 14.4 ± 2 | 2.5 ± 1 |
| CBB-20 | 14.5 ± 1 | 3.1 ± 2 |
| CBB-30 | 14.3 ± 1 | 3.6 ± 1 |
| LNE | 15.6 ± 1 | 5.2 ± 1 |
| LNE-1 | 15.1 ± 2 | 5.1 ± 2 |
| LNB-3 | 15.2 ± 1 | 3.8 ± 1 |

Experiment 17

Figure 5:
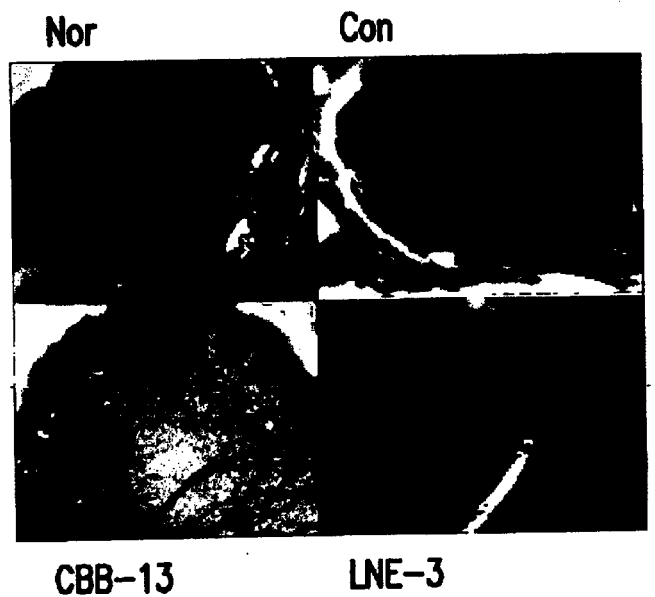
FIG. 5 shows the number and distribution pattern of CAM observed for 3 days by treating the fertilized egg with the effective component as the organic solvent extract in the concentration of 10 µg/ml, incubating the egg in an incubator at 37° C. for 2 days and then carefully injecting $5 \times 10^3$ synovial cells on CAM via syringe.

The extractions obtained as in Experiment 3 were observed for the effect on angiogenesis of synovial cells in terms of the extent of CAM reduction. As a result thereof, it could be seen that normal fertilized eggs somewhat slowly induced the CAM formation and the cells into which synovial cells were injected strongly induced the CAM formation, whereas the group treated with LNE-3 fraction more strongly inhibited the induction of CAM formation in comparison to the control group. Therefore, in view of the fact that the composition of the present invention inhibits not only the proliferation of synovial cells but also the CAM induction of angiogenesis by synovial cells, it can be noted that the composition of the present invention has a good effect for treatment of arthritis (FIG. 5)

EXAMPLE 18

Figure 6:
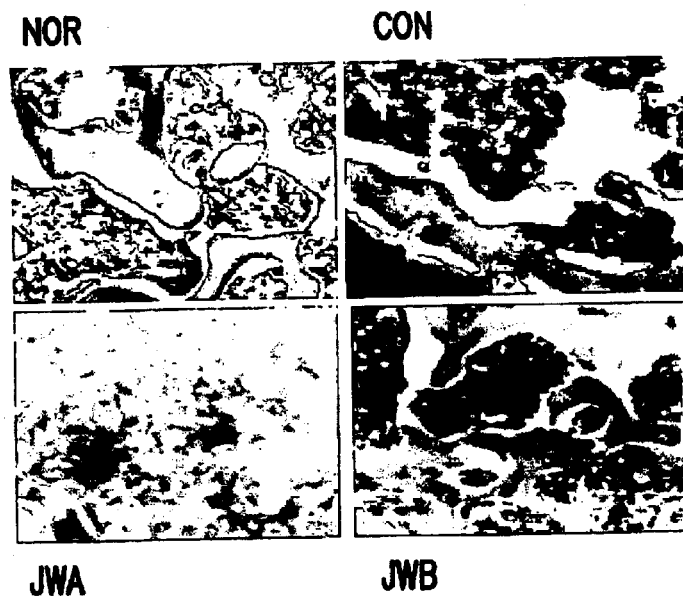
FIG. 6 is H/E tissue staining which shows the rupture extent of cartilaginous tissue after 70 days from the treatment of arthritis-induced animal with the water extract of the pharmaceutical composition at the concentration given in FIG. 9.

As shown in Experiment 4, the cartilage portion was stained with hematoxylin/eosin and then observed and photographed with a phase-contrast microscope of 100 magnifications to identify the abrasive condition of cartilage present in joint portion and the rupture extent of cartilage tissue and cartilage cells due to secretion of metalloprotease. As a result thereof, it could be noted that the normal group showed a uniform distribution pattern of cartilage tissue and the control group showed much bone rupture and the traces of osteolysis, whereas JWA and JWB showed the similar pattern of bone tissue in comparison to the normal group. This suggests that the water extract of the present invention has an activity for rupture and regeneration of cartilage tissues (FIG. 6).

Experiment 19

Figure 7A:
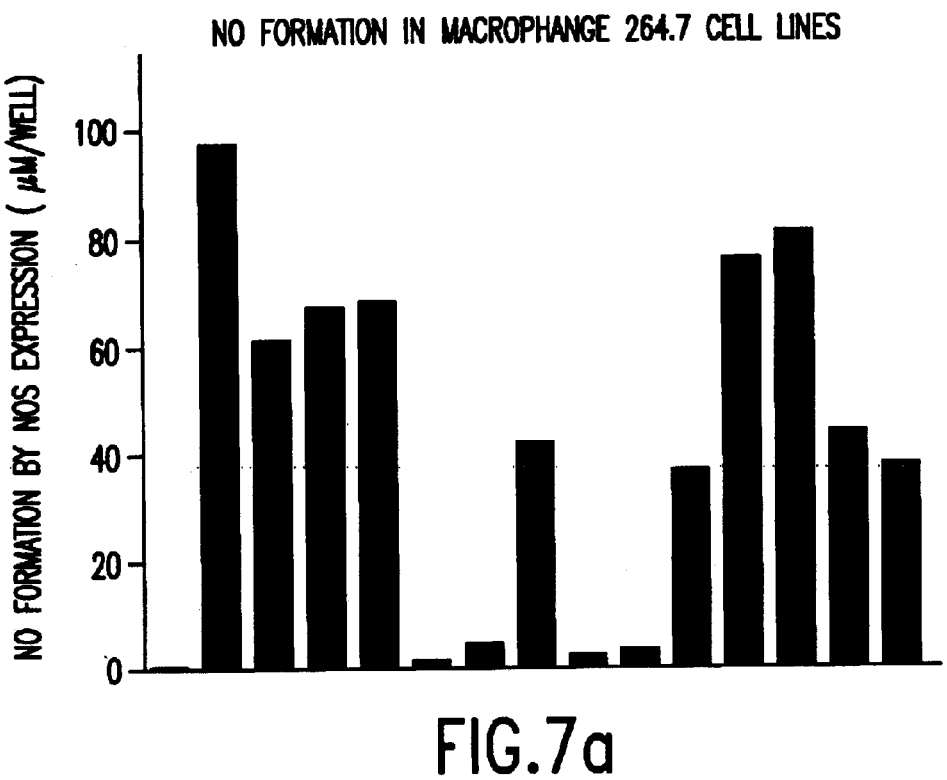
FIG. 7 is (a) a bar graph showing the inhibition of NO formation when Raw 264.7 cell lines are treated with the organic solvent fraction of a single drug of the pharmaceutical composition at the concentration of 10 µg/ml for 24 hours an then stimulated with LPS, and (b) a bar graph showing the inhibition of NO formation when the cell lines treated with CBB fraction and LNE fraction as the organic solvent fractions are stimulated with LPS according to the same manner as above (a).
Figure 7B:
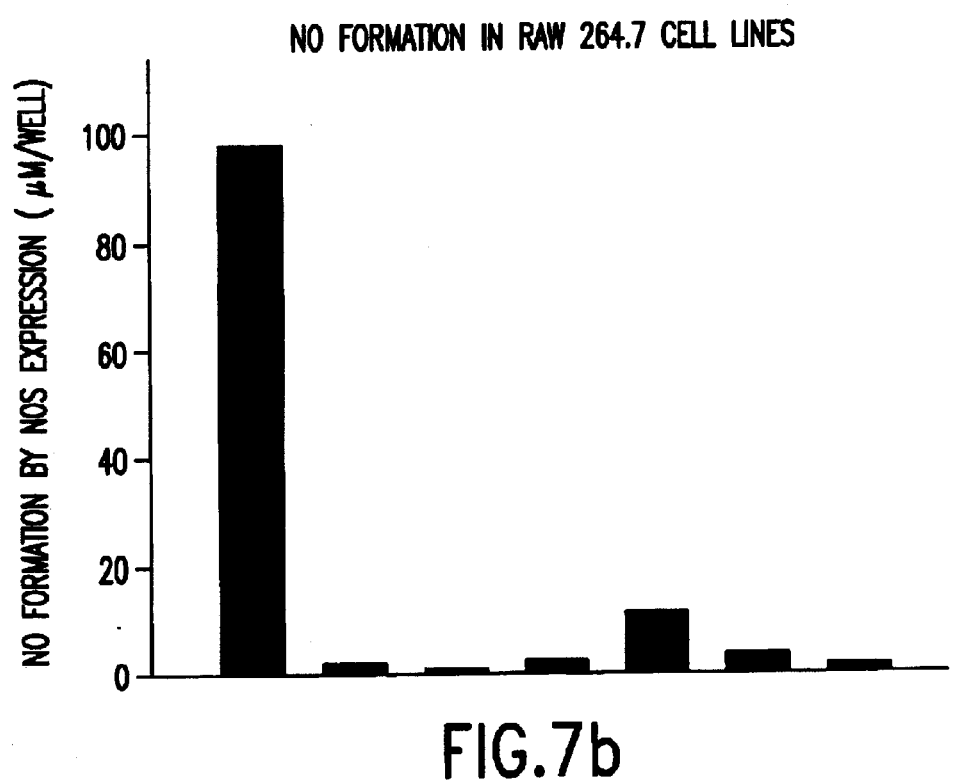

The effect of the fractions of the present invention was comparatively analyzed as in Experiment 5 above and then analogized by a relative estimation from the obtained data to obtain the result as represented in the bar graph of FIG. 7. Specifically, it could be seen that the control group shows a relatively high NO formation of about 98 μM per well whereas the groups treated with fractions CBB, CBE, LNE and LNB exhibit a significant inhibition of NO formation (FIG. 7a). Particularly, it could be seen that a series of LNE fractions and LNE-3 exhibit a stronger inhibitory effect on NO formation. It is considered that this result is caused by inhibition of the composition of the present invention on the synthesis of iNOS, which induces the NO formation (FIG. 7b).

Experiment 20

Figure 8A:
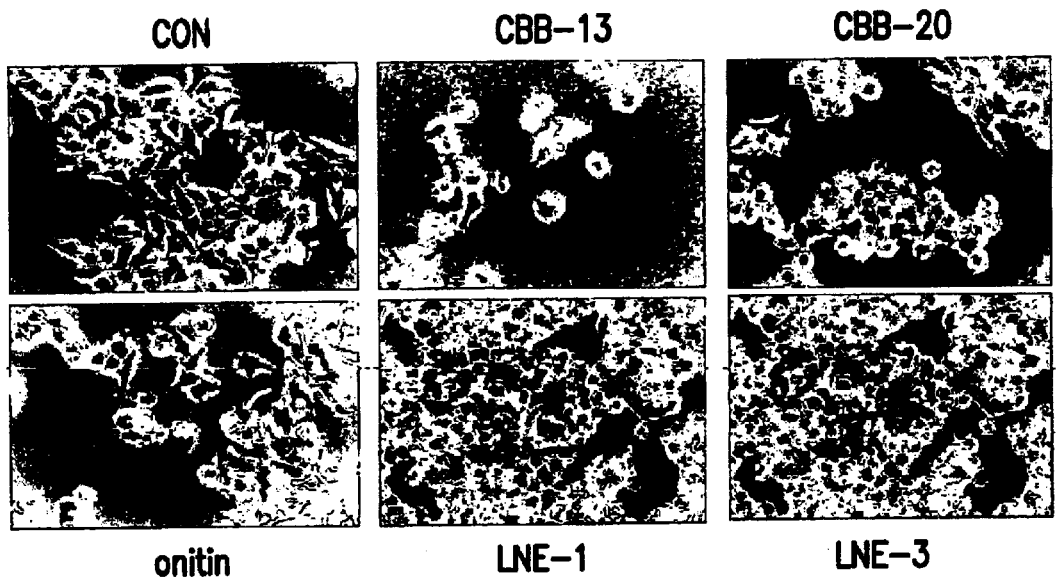
FIG. 8 shows (a) the induction pattern of apoptosis when Raw 264.7 cell lines are treated with the organic fraction of the effective component at the concentration of about 20 □g/ml and then stimulated with LPS, and (b) the result of observing whether the synovial cells show the same pattern according to the same method as above (a).
Figure 8B:
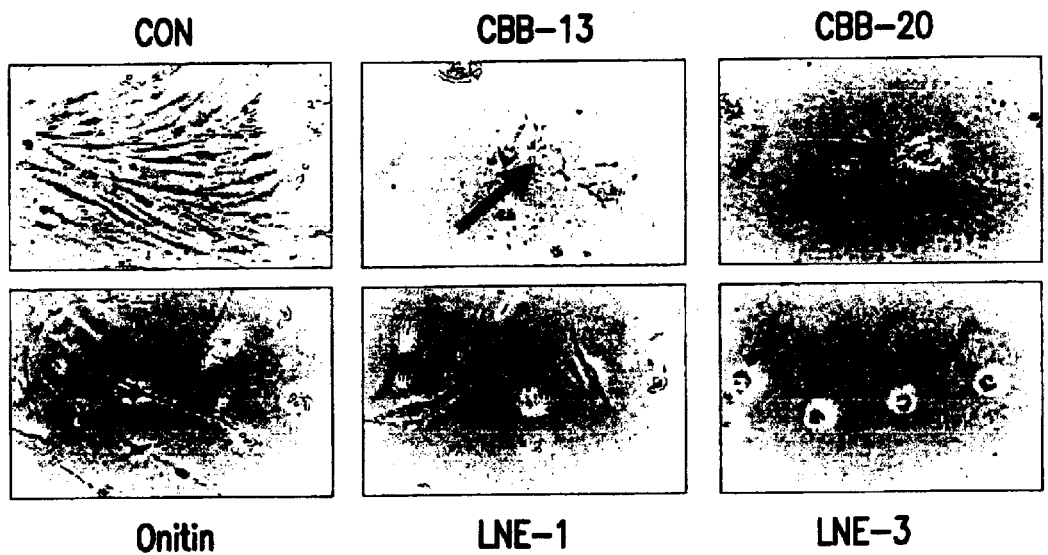

As in Experiment 6, it has been examined whether the compound of the present invention can induce the apoptosis of Raw 264.7 cell lines as macrophage and synovial cells. As the result thereof, it could be seen that the control group actively progressed the cell proliferation whereas the drug-treated groups exhibited an effect of more strongly inducing the apoptosis, particularly in case of LNE-1 and 3 as a series of LNE fractions. Therefore, it is considered that the composition of the present invention induces the apoptosis of two kinds of cell lines as tested, and consequently, is concerned in the inhibition of inflammation and edema (FIGS. 8a, b).

Experiment 21

Figure 9A:
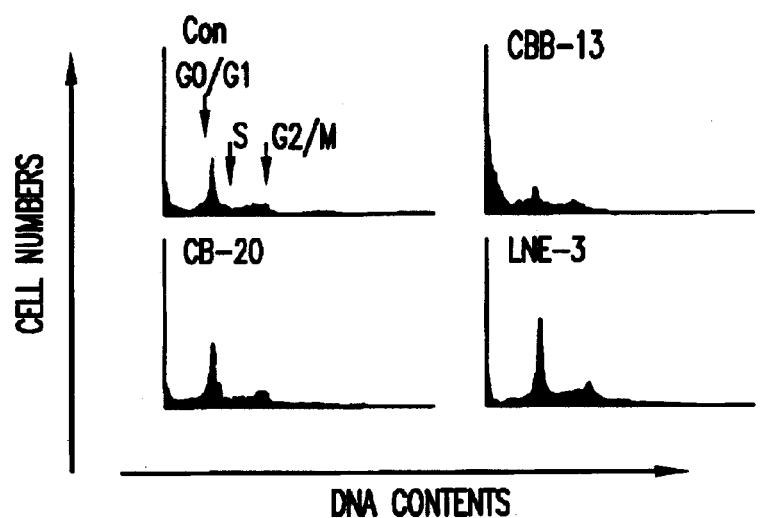
FIG. 9 shows (a) the result of flow cytometry to determine the effect on cell cycle by treating Raw 264.7 cell lines with the organic fraction of the effective component at the concentration of about 20 µg/ml and then stimulating with LPS and (b) the result of observing whether the synovial cells show the same appearance according to the same method as above (a).
Figure 9B:
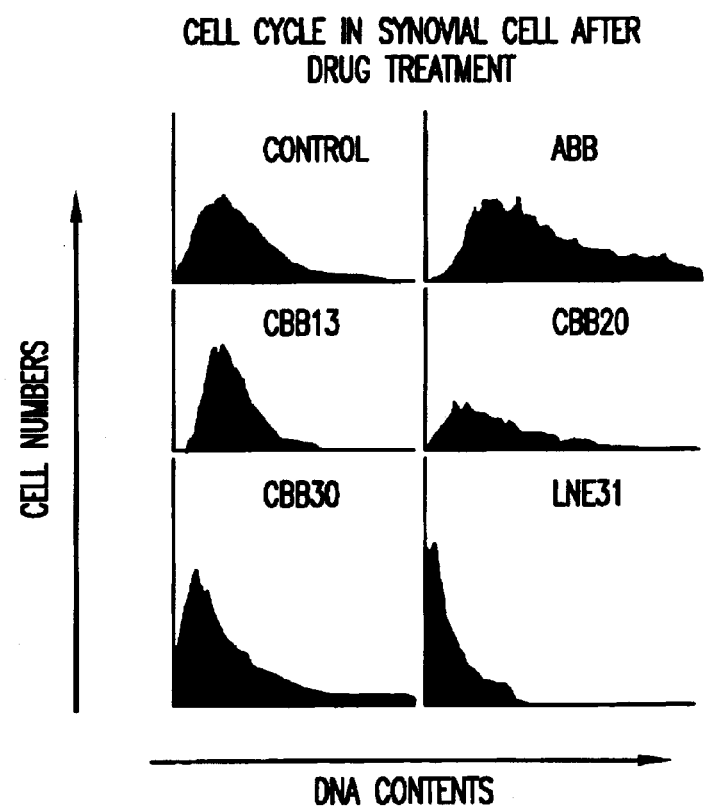

In the above Experiment 7, the effect of the active fractions as the pharmaceutical composition of the present invention on the cell cycle was observed using synobial fibroblast cell lines and Raw 264.7 cell lines as macrophage. As the result thereof, it could be noted that in case of macrophage cell lines the control group typically showed the relatively highest peak at $G_0/G_1$ phase, the lowest peak at S phase and the medium peak at $G_2/M$ phase. In the drug-treated groups, in view of the fact that CBB-13 induced the apoptosis and LNE-2 induced $G_0/G_1$ arrest, it is believed that these tested fractions are a drug inducing the apoptosis (FIG. 9a). Meanwhile, in case of synovial cell lines, the control group usually showed differently from the actively proliferating cell lines that the peak at $G_0/G_1$ phase of cells is relatively lower than that at $G_2/M$ phase and S phase of cells generally showed a high peak. This is the cell pattern as can be seen in metastatic cancer cells occurring much karyomitosis more than cell division and having a slow proliferation rate, or cells occurring angiogenesis. In view of the fact that as the fractions of the present invention CBB-13 showed the pattern of $G_0/G_1$ arrest and LNE-3 induced the apoptosis, they are regarded as being a drug inducing the apoptosis in synovial cells (FIG. 9b). Therefore, it can be seen that LNE-3 as the fraction according to the present invention induces the apoptosis to inhibit the cell proliferation as the cause of bone diseases and therefore, has a significant effect in treating bone diseases.

Experiment 22

Figure 10:
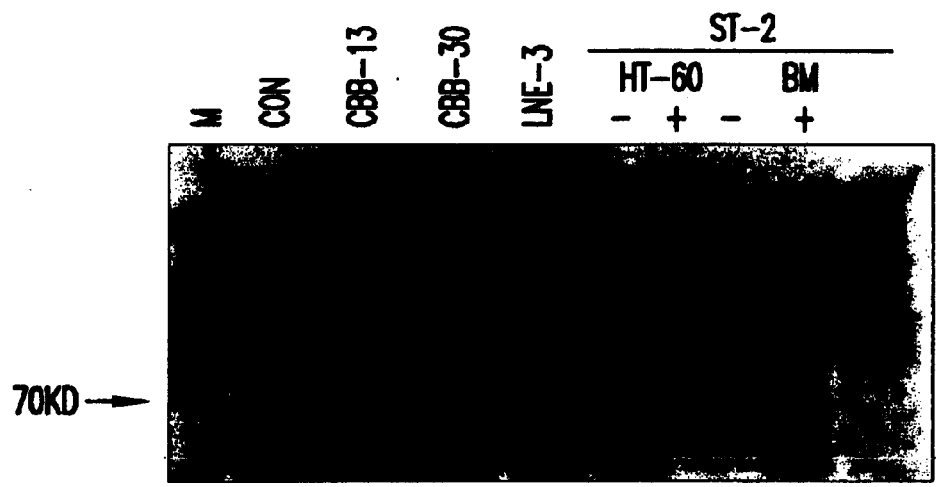
FIG. 10 shows the inhibitory effect on the expression of COX-II enzyme protein as measured by SDS-PAGE electrophoresis when synovial cell lines are treated with the organic fraction of the effective component and then stimulated with LPS.

As in Experiment 11, the pharmaceutical composition of the present invention was observed whether the effective component thereof inhibits the expression of COX-II as the cause of rheumatoid arthritis in synovial cells, by electrophoresis on 10% polyacrylamide gel (SDS-PAGE), staining and then decoloring with the destaining solution. As the result thereof, the molecular weight of COX-II protein was determined as about 70 KD, and in view of the fact that the control group showed a strong band whereas LNE-3 group showed a weak band, it could be noted that the drug of the present invention has a pharmacological activity for inhibiting the protein expression (FIG. 10).

Experiment 23

Figure 11A:
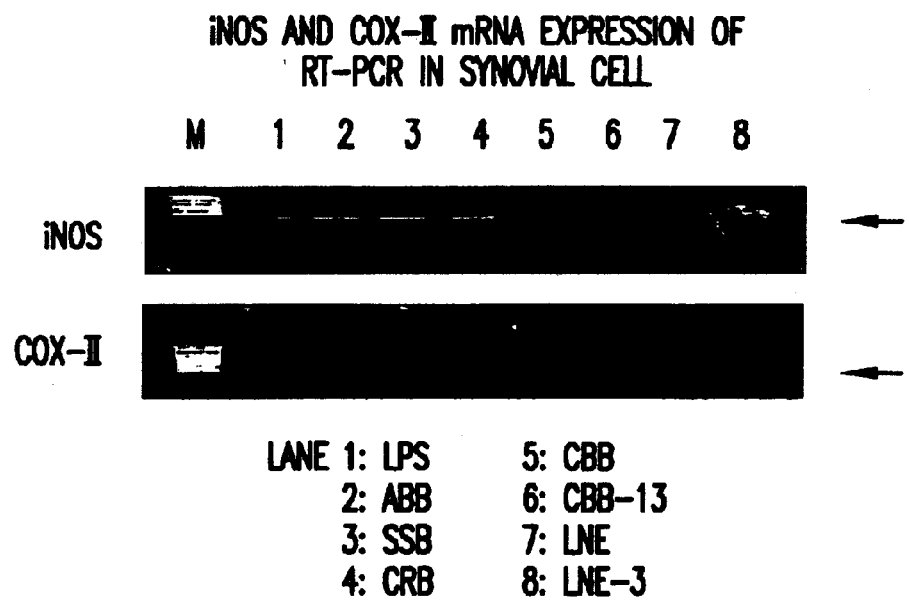
FIG. 11 shows the inhibitory effect on the synthesis of iNOS and COX-II enzymes as measured by RT-PCR when synovial cell lines are treated with the organic fraction of the effective component and then stimulated with LPS, and the inhibitory effect of respective fractions on the synthesis of iNOS (b) and COX-II (c) enzymes according to the same method as above (a).
Figure 11B:
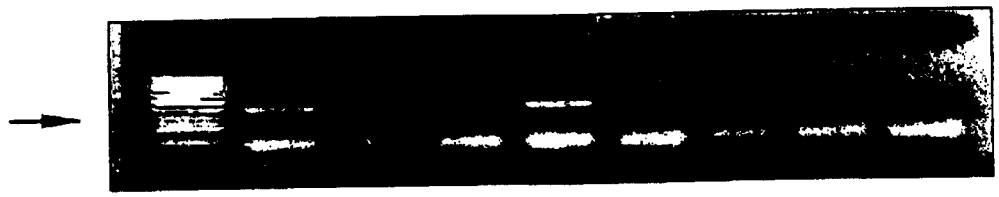
Figure 11C:
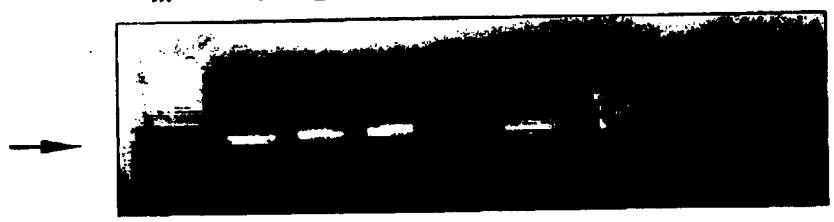

By practicing PCR and electrophoresis as in Experiment 8, it was identified whether PCR product has the band near 278 bp in case of iNOS. As the result, it could be identified that lanes 1, 2, 3 and 4 are the control group and ABB, SSB and CRB groups, respectively, and have no effect on the protein expression, whereas lanes 5, 6, 7 and 8 are CBB, CBB-13, LNE and LNE-3 groups, respectively, and have an effect on the protein expression. In case of COX-II, lanes 1, 2 and 3 have no effect on the protein expression whereas lanes 4, 5, 6, 7 and 8 showed an inhibitory effect at the level of transcription (FIG. 11a). Further, as in Experiment 15, it was examined whether the fractions used as the effective component in the pharmaceutical composition of the present invention has any effect on the expression of COX-II and iNOS as the cause of rheumatoid arthritis. As the result thereof, in case of iNOS protein, it could be seen that lanes 1, 3 and 4 as the elute lanes for respective fractions are the control group and ABB and CRB groups, respectively, and have no effect on the protein expression whereas lanes 2, 5, 6, 7 and 8 are CBB, LNE, SD, DS and YM groups, respectively, and strongly inhibit the protein expression (FIG. 11b). Further, in case of COX-II it could also be identified that lanes 1, 2, 3 and 5 are the control group and CBW, ABB and LNW groups, respectively, and have no effect on the protein expression whereas lanes 4, 6, 7 and 8 are CBB-13 and 20 and LNE-1 and 3 groups, respectively, and strongly inhibit the protein expression (FIG. 11c).

Experiment 24

Figure 12:
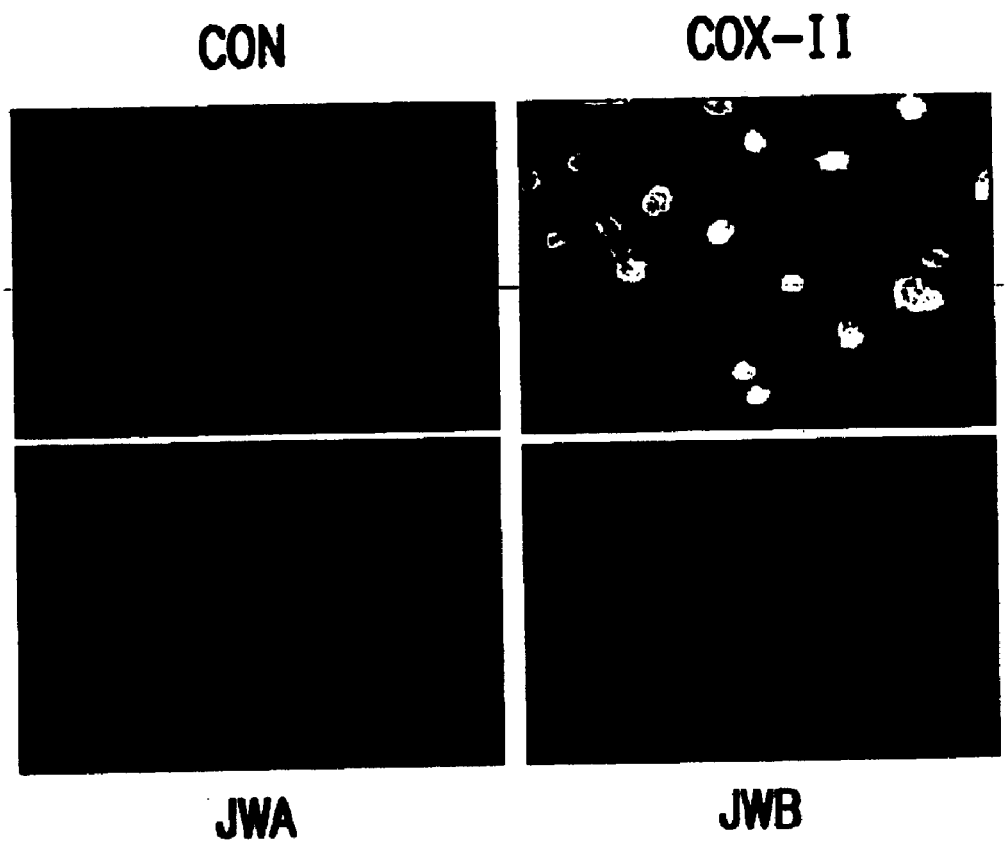
FIG. 12 shows the result obtained by labeling synovial cell lines with a secondary antibody FITC, allowing to stand the cells for about one hour while shading the light with a foil and then observing the cells under a fluorescence microscope, in order to examine whether the compound identified as the effective component in the pharmaceutical composition of the present invention can induce the inhibitory effect on COX-II expression in synovial cells in joint portion.

In order to determine whether the pharmaceutical composition separated by the present invention induces the inhibitory effect on COX-II of synovial cells in joint portion, as in Experiment 10, the cells were fixed by dropping methanol above the cells and then washed with PBS. The cells were labeled with the primary antibody COX-II and then allowed to stand at 4° C. for about one hour. Then, the cells were labeled with FITC as the secondary antibody, allowed to stand for about one hour while masking from light with foil and then observed under a fluorescence microscope. As the result thereof, it could be seen that the control group more strongly expressed COX-II protein in comparison to the normal group whereas LNE-3 group showed a tendency to greatly decrease the protein expression. It is considered that this result is caused by inhibition of COX-II protein expression at the level of transcription as like as Experiment 16 (FIG. 12).

Experiment 25

In order to observe the inhibitory effect on edema of the pharmaceutical composition of the present invention, edema-induced albino rats were treated with LNE-1 and 3 as the separated organic solvent extracts, respectively, and then anesthetized to take X-ray photograph. As the result thereof, in the control group, the cartilage portion invaded with rheumatoid arthritis was seriously ruptured and bone tissue was severely damaged and further, the extent of such damage reached the peak level until about 70 days has passed.

Figure 13:
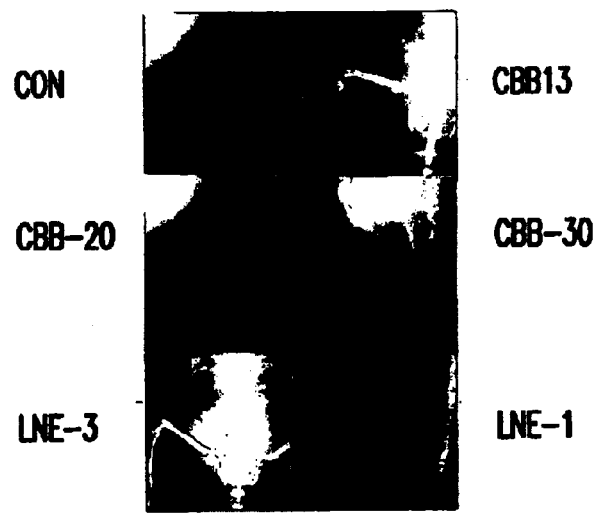
FIG. 13 is X-ray photograph to show the 70-days inhibitory effect on edema as one of chronic and degenerative osteopathological symptoms of arthritis by treating the induced edema with respective fractions obtained as the organic solvent fractions of the pharmaceutical composition in an amount of 75 µg/ml for 2 weeks via oral route.

Contrary to the control group, it could be seen that LNE-3 inhibits the rupture of cartilage in arthritic portion and has an effect of stimulating the osteogenesis (FIG. 13).

Experiment 26

Figure 14:
FIG. 14 is the result of computerized tomography (CT) to show the clinical improvement in an outpatient suffering from ruptured disc with the pharmaceutical composition of the present invention.

In order to examine the clinical pharmacological effect of the pharmaceutical composition separated and purified as in Experiment 12, the water extract obtained according to the present invention was administered for 2 months to a patient suffering from ruptured disc and then, the patient was observed by CT photographing before and after treatment with the extract of the present invention. As the result thereof, the control group occurred the rupture of disc before treatment whereas after treatment, showed the elimination of disc and neuritis, and thus, also removed neuroparalysis due to neuritis (FIG. 14).

Experiment 27

Figure 15:
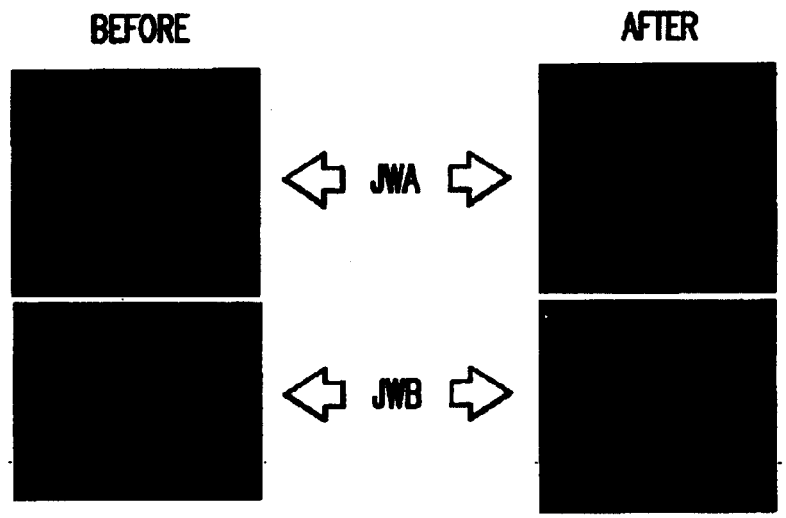
FIG. 15 is the result of magnetic resonance imaging (MRI) to show the clinical improvement in an outpatient suffering from ruptured disc with the pharmaceutical composition of the present invention.
Figure 16:
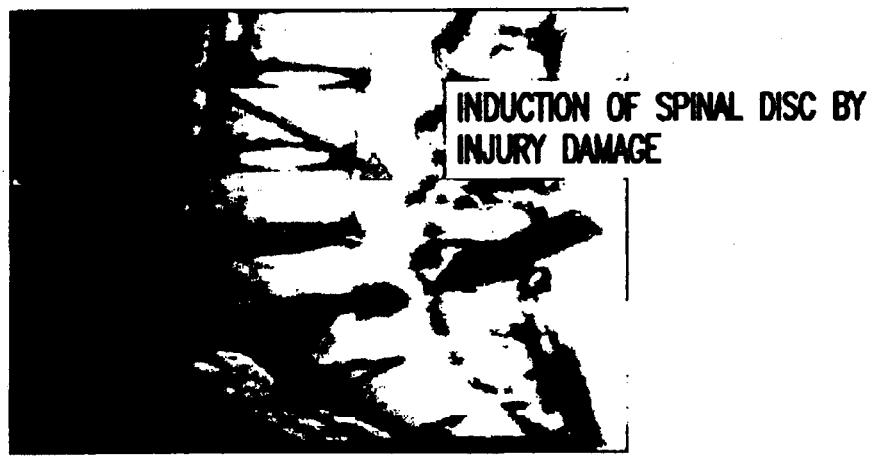
FIG. 16 shows the presence of nogo-A with respect to the mechanism to induce vertebral neuroparalysis in an outpatient suffering from ruptured disc.
Figure 17:
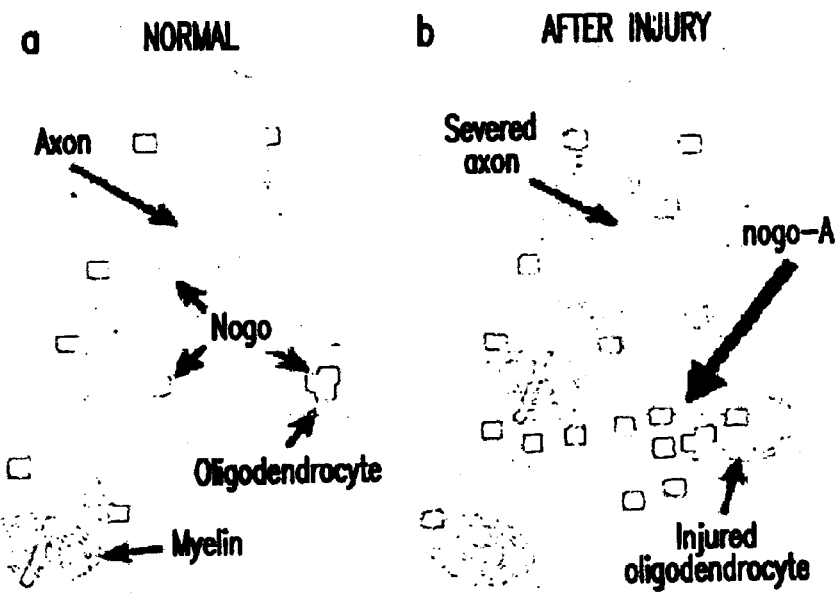
FIG. 17 shows a channel for blocking neurotransmission by raising the injury in oligodendrocyte present around the axon as the nervous portion concerned with a paralysis of neurotransmission.

The patient suffering from ruptured disc was treated with the water extract obtained in Experiment 1 and then observed by MRI photographing. The control group occurred the rupture of disc before treatment but showed the elimination of disc and also removed neuroparalysis, after treatment (FIG. 15).

Experiment 28

Figure 18B:
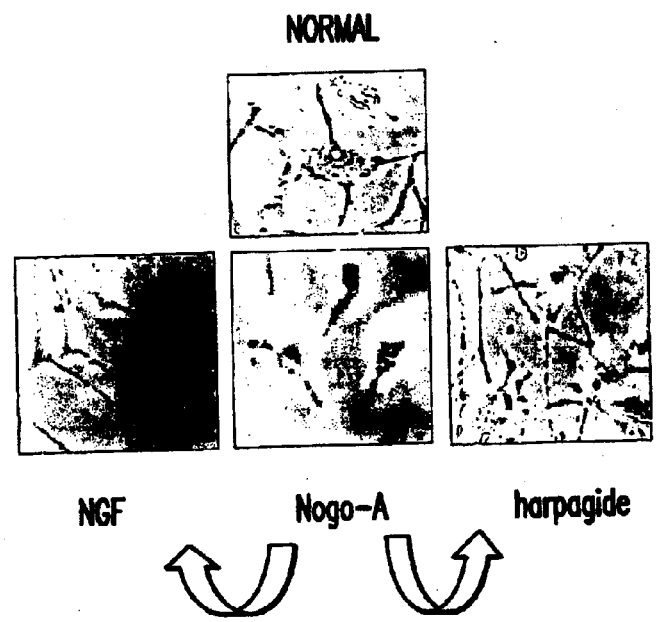
FIG. 18 shows (a) a channel for blocking neurotransmission to brain cells as in case that the injury is raised in oligodendrocyte present around the axon as the nervous portion concerned with a paralysis of neurotransmission, (b) the recovery of neurotransmission by treating cells with NGF or CBB-13/LNE-2 to regenerate neutrite, which recovers the neurotransmission.
Figure 18A:
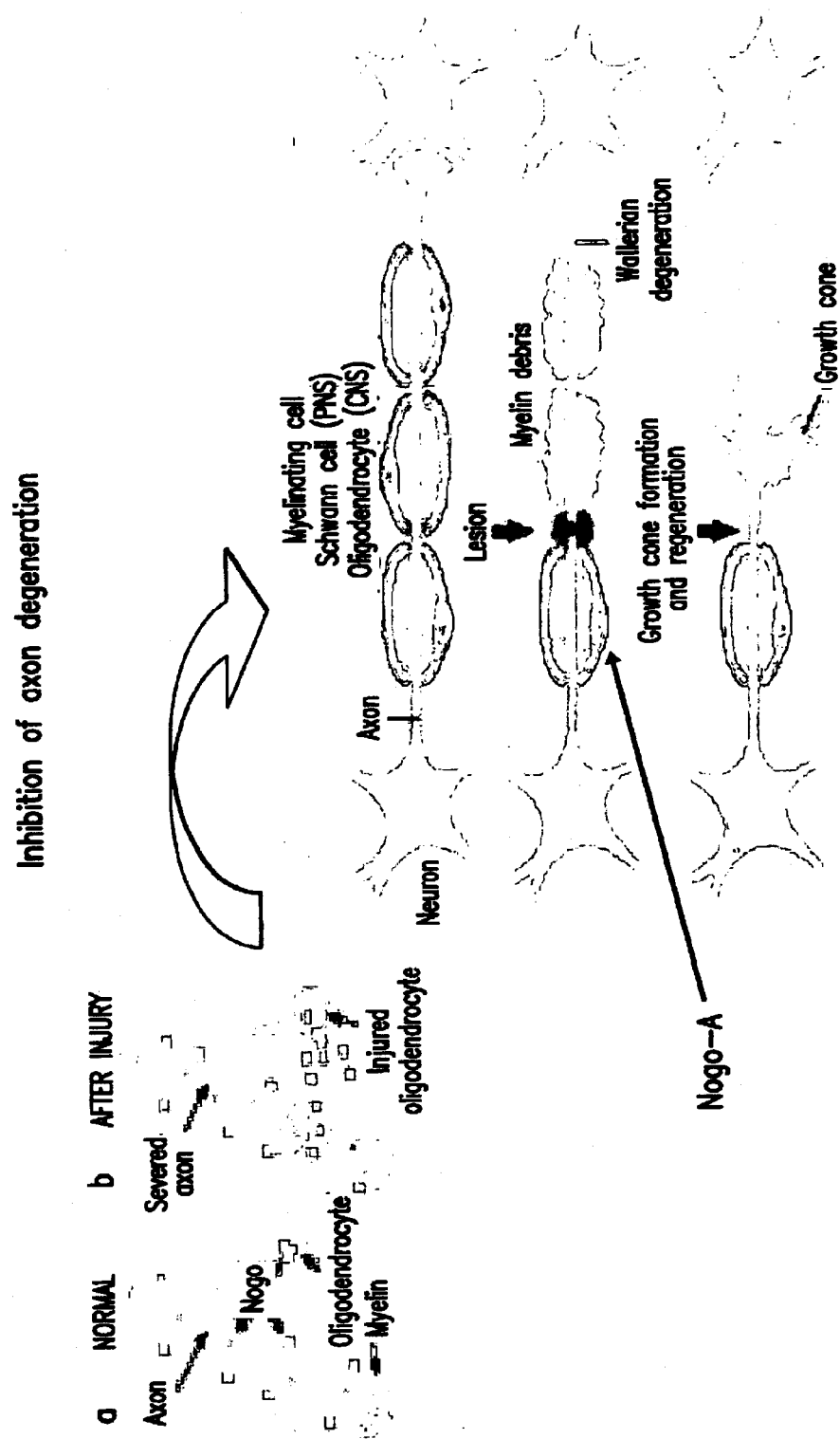

As in Experiment 16, it was observed whether the fractions of the present invention reduces or inhibits neurites of nerve and at the same time, identified whether neurites can be regenerated by treatment with neuronal growth factor (NGF) or whether the fractions of the present invention can provide the same effect, by taking a photograph with a phase-contrast microscope of 200 magnifications. As the result thereof, it could be seen that nogo-A expressed U-373 cell lines show the pattern that originally long-extended neurites were reduced or substantially eliminated (FIG. 18a) whereas in case of treatment with CBB13 and LNE-3 the cells shows the pattern that neurites were lengthened. From such finding, it is considered that the composition of the present invention stimulates the regeneration of neurites to regenerate the nerve, in comparison to NGF (FIG. 18b).

Experiment 29

According to determination of chemical structures of the compounds exhibiting the effects on bone diseases, which were separated and identified as the effective component of the pharmaceutical composition according to the present invention, it was identified that LNE-1 and 3 are harpagoside and harpagide, respectively, of which the chemical identification has been already established. However, their pharmacological effects were never identified before the present invention and first clarified in the present invention by the results of above experiments.

As confirmed by the above experimental results, harpagide and harpagoside of the present invention have an effect for treating osteoporosis, arthritis and ruptured disc.

Therefore, the compounds of the present invention can be effectively used as a medicine.

Although the dosage of the compounds of the present invention can be varied depending on sex and age of patients, severity of the concerned disease, etc., in general a daily dosage of 0.1 mg to 500 mg can be administered once or in a multiply divided dose.

The compounds of the present invention can be used in combination with prior drugs which have been used for prevention and treatment of osteoporosis and arthritis, for example, allendrate, tamoxifen, vitamin $D_3$, parathyroid hormone (PTH), sulfasalazine, thioredoxin reductase, alendronate, raloxifene, calcitonin, estradiol, genistein, 1,25-dihydroxyvitamin $D_3$, alendronate, estrogen receptor modulator, biphosphonates, or shinbarometin (a drug of which the use was developed by the present inventors).

By combining the compounds of the present invention with the prior drugs as above, the common dosage of the prior drugs can be decreased so that the problems involved in the prior drugs can be diminished.

The compounds of the present invention can be formulated into a pharmaceutical preparation by mixing the compounds with an excipient, an auxiliary, an agent for removing pain, an isotonic agent, a preservative and the others, which are conventionally used in pharmaceutical field, and then formulating the mixture in the form of a pharmaceutically acceptable preparation. Such pharmaceutical preparations include injections, solutions, tablets, capsules, powders, syrups, etc.

The present invention will be more specifically explained by the following preparation examples.

Preparation Example 1

| | |
|---|---|
| Harpagide | 5 mg |
| Sterilized, distilled water for injection | q.s. |
| Agent for adjusting pH | q.s. |

Harpagide was dissolved in distilled water for injection and adjusted to pH of about 7.6 using an agent for adjusting pH. The total volume was made to 2 ml, filled in a 2 ml ampoule and then sterilized to prepare an injectable preparation.

Preparation Example 2

| | |
|---|---|
| Harpagoside | 10 mg |
| Sterilized, distilled water for injection | q.s. |
| Agent for adjusting pH | q.s. |

Harpagoside was dissolved in distilled water for injection and adjusted to pH of about 7.2 using an agent for adjusting pH. The total volume was made to 2 ml, filled in a 2 ml ampoule and then sterilized to prepare an injectable preparation.

Preparation Example 3

| | |
|---|---|
| Harpagide | 20 mg |
| Lactose | 100 mg |
| Starch | 100 mg |
| Magnesium stearate | q.s. |

The above-indicated components were mixed and then compressed according to the conventional method for preparing tablets to produce a tablet preparation.

Preparation Example 4

| | |
|---|---|
| Harpagide | 10 mg |
| Harpagoside | 10 mg |
| Lactose | 100 mg |
| Starch | 50 mg |
| Magnesium stearate | q.s. |

The above-indicated components were mixed and then compressed according to the conventional method for preparing tablets to produce a tablet preparation.

Preparation Example 5

| | |
|---|---|
| Harpagide | 15 mg |
| Lactose | 50 mg |
| Starch | 50 mg |
| Talc | 2 mg |
| Magnesium stearate | q.s. |

The above-indicated components were mixed and then filled in a suitable gelatin capsule according to the conventional method for preparing capsules to produce a capsule preparation.

Preparation Example 6

| | |
|---|---|
| Harpagide | 25 mg |
| Lactose | 100 mg |
| Starch | 93 mg |
| Talc | 2 mg |
| Magnesium stearate | q.s. |

The above-indicated components were mixed and then filled in a suitable gelatin capsule according to the conventional method for preparing capsules to produce a capsule preparation.

Preparation Example 7

| | |
|---|---|
| Harpagoside | 500 mg |
| Sugar | 20 g |
| Isomerized sugar | 20 g |
| Lemon flavor | q.s. |
| Add purified water | to make 100 ml. |

The above-indicated components were mixed according to the conventional method for preparing liquid preparations, and then filled in a 100 ml brown bottle and sterilized to produce a solution preparation.

Preparation Example 8

| | |
|---|---|
| Harpagide | 100 mg |
| Shinbarometin | 100 mg |
| Sugar | 20 g |
| Isomerized sugar | 20 g |
| Lemon flavor | q.s. |
| Add purified water | to make 100 ml. |

The above-indicated components were mixed according to the conventional method for preparing liquid preparations, and then filled in a 100 ml brown bottle and sterilized to produce a solution preparation.

Preparation Example 9

| | |
|---|---|
| Harpagide | 5 mg |
| Allendrate | 10 mg |
| Sterilized, distilled water for injection | q.s. |
| Agent for adjusting pH | q.s. |

Harpagide and allendrate were dissolved in distilled water for injection and adjusted to pH of about 7.6 using an agent for adjusting pH. The total volume was made to 2 ml, filled in a 2 ml ampoule and then sterilized to prepare an injectable preparation.

Preparation Example 10

| | |
|---|---|
| Harpagide | 5 mg |
| Tamoxifen | 10 mg |
| Sterilized, distilled water for injection | q.s. |
| Agent for adjusting pH | q.s. |

Harpagide and tamoxifen were dissolved in distilled water for injection and adjusted to pH of about 7.6 using an agent for adjusting pH. The total volume was made to 2 ml, filled in a 2 ml ampoule and then sterilized to prepare an injectable preparation.

Preparation Example 11

| | |
|---|---|
| Harpagoside | 20 mg |
| Sulfasalazine | 20 mg |
| Lactose | 100 mg |
| Starch | 100 mg |
| Magnesium stearate | q.s. |

The above-indicated components were mixed and then compressed according to the conventional method for preparing tablets to produce a tablet preparation.

Preparation Example 12

| | |
|---|---|
| Harpagoside | 20 mg |
| Allendronate | 50 mg |
| Lactose | 100 mg |
| Starch | 50 mg |
| Magnesium stearate | q.s. |

The above-indicated components were mixed and then compressed according to the conventional method for preparing tablets to produce a tablet preparation.

Preparation Example 13

| | |
|---|---|
| Harpagide | 10 mg |
| Shinbarometin | 10 mg |

-continued

| | |
|---|---|
| Lactose | 50 mg |
| Starch | 50 mg |
| Talc | 2 mg |
| Magnesium stearate | q.s. |

The above-indicated components were mixed and then filled in a suitable gelatin capsule according to the conventional method for preparing capsules to produce a capsule preparation.

Preparation Example 14

| | |
|---|---|
| Harpagide | 5 mg |
| Raloxifene | 10 mg |
| Lactose | 50 mg |
| Starch | 50 mg |
| Talc | 2 mg |
| Magnesium stearate | q.s. |

The above-indicated components were mixed and then filled in a suitable gelatin capsule according to the conventional method for preparing capsules to produce a capsule preparation.

Preparation Example 15

| | |
|---|---|
| Harpagide | 5 mg |
| Disodium pamidronate | 20 mg |
| Lactose | 100 mg |
| Starch | 93 mg |
| Talc | 2 mg |
| Magnesium stearate | q.s. |

The above-indicated components were mixed and then filled in a suitable gelatin capsule according to the conventional method for preparing capsules to produce a capsule preparation.

Preparation Example 16

| | |
|---|---|
| Harpagide | 1000 mg |
| Disodium pamidronate | 1000 mg |
| Sugar | 20 g |
| Isomerized sugar | 20 g |
| Lemon flavor | q.s. |
| Add purified water | to make 100 ml. |

The above-indicated components were mixed according to the conventional method for preparing liquid preparations, and then filled in a 100 ml brown bottle and sterilized to produce a solution preparation.

Industrial Applicability

It has been identified that the compound represented by formula (I), as defined above, according to the present invention has a potent effect for treating osteoporosis, arthritis and ruptured disc. Therefore, the pharmaceutical composition containing this compound as an effective component can be effectively used for prevention and treatment of osteoporosis, arthritis and ruptured disc.

What is claimed is:

1. A method of treating arthritis, osteoporosis and ruptured disc comprising administering to a patient in need thereof a pharmaceutically acceptable amount of the compound of formula (I):

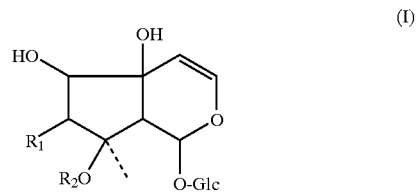

in which

R1 represents a hydrogen atom or an alkyl group; and

R2 represents a hydrogen atom; and

Glc represents glucose; along with a pharmaceutically acceptable adjuvant.

2. A pharmaceutical preparation containing as an effective component a compound represented by the following formula (I):

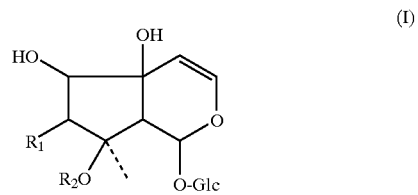

in which $R_1$ represents a hydrogen atom or an alkyl group and $R_2$ represents a hydrogen atom, and Glc represents glucose wherein the pharmaceutical preparation has a potent effect against osteoporosis, arthritis and ruptured disc and the compound represented by formula (1) is present in a concentration amount of from 2.5 to 5 mg compound per ml composition.

3. A pharmaceutical preparation containing as an effective component a compound represented by the following formula (I):

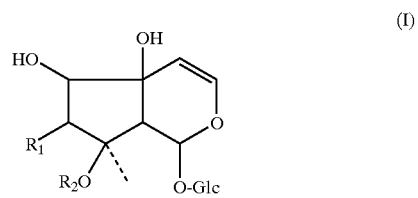

in which $R_1$ represents a hydrogen atom or an alkyl group and $R_2$ represents a hydrogen atom, and Glc represents glucose and one or more materials selected from the group consisting of allendrate, tamoxifen, vitamin $D_3$, parathyroid hormone (PTH), sulfasalazine, thioredoxin reductase, alendronate, raloxifene, calcitonin, estradiol, genistein, 1,25-dihydroxyvitamin $D_3$, biphosphonates, shinbarometin and shinbarometin acetate wherein said pharmaceutical preparation has a potent effect against osteoporosis, arthritis and ruptured disc.

* * * * *